United States Patent [19]

Attie et al.

[11] Patent Number: 5,646,113
[45] Date of Patent: Jul. 8, 1997

[54] TREATMENT OF PARTIAL GROWTH HORMONE INSENSITIVITY SYNDROME

[75] Inventors: Kenneth Attie, San Francisco, Calif.; Lena Mariana Susann Carlsson, Gothenburg, Sweden; Neil Gesundheit, Los Altos; Audrey Goddard, San Francisco, both of Calif.

[73] Assignee: Genentech, Inc., South San Francisco, Calif.

[21] Appl. No.: 224,982

[22] Filed: Apr. 7, 1994

[51] Int. Cl.$^6$ .......................... A61K 14/00; A61K 38/27; A61K 38/14
[52] U.S. Cl. .......................... 514/12; 530/303; 530/311; 530/399
[58] Field of Search .................. 514/12, 21; 530/311, 530/303, 399

[56] References Cited

U.S. PATENT DOCUMENTS 5,126,324 6/1992 Clark et al. .................. 514/21

OTHER PUBLICATIONS

Rosenfeld et al., "Growth Hormone (GH) Insensitivity" Receptor Deficiency, *Endocrine Reviews* 15 (3):369–90 (1994).

Aguirre et al., "High–Affinity Serum Growth–Hormone–Binding Protein, Absent in Laron–Type Dwarfism, is Diminished in Heterozygous Parents" *Horm. Res.* 34:4–8 (1990).

Amselem et al., "Spectrum of Growth Hormone Receptor Mutations and Associated Haplotypes in Laron Syndrome" *Hormone Molecular Genetics* 2 (4) :355–359 (1993).

August et al., "Growth Hormone Treatment in the United States: Demographic and Diagnostic Features of 2331 Children" *J. Pediatr.* 116 (6) :899–903 (1990).

Blum et al., "Improvement of Diagnostic Criteria in Growth Hormone Insensitivity Syndrome: Solutions and Pitfalls" *Acta Paediatr. Suppl.*, B. Lippe et al., Lisbon, Portugal vol. 399:117–124 (Presented Oct. 1993).

Carlsson et al., "Reduced Concentration of Serum Growth Hormone–Binding Protein in Children with Idiopathic Short Stature" *J. Clin. Endocrinol. and Metab.* 78 (6) :1325–1330 (1994).

Eshet et al., "Defect of Human Growth Hormone Receptors in the Liver of Two Patients with Laron–Type Dwarfism" *Is. J. Med. Sci.* 20:8–11 (1984).

Fine et al., "Growth After Recombinant Human Growth Hormone Treatment in Children with Chronic Renal Failure: Report of a Multicenter Randomized Double–Blind Placebo–Controlled Study" *J. Pediat.* 1241(3) :374–382 (March 1994).

Gillespie et al., "Enhanced Potency of Truncated Insulin–Like Growth Factor–I (des (1–3) IGF–I) Relative to IGF–I in lit/lit mice" *J. Endocrinol.* 127:401–405 (1990).

Goddard et al., "Growth Hormone (GH) Receptor Defects are Present in Selected Children with Non–GH–Deficient Short Stature: A Molecular Basis for Partial GH–Insensitivity" *Proc. 76th Ann. Meeting of Endocrine Soc.* pp. 204 (Jun. 1994).

Hayek et al., "Growth and Somatomedin–C Responses to Growth Hormone in Dwarfed Children" *J. Pediatrics* 99 (6) :868–872 (1981).

Kou et al., "Amino Acid Substitutions in the Intraceullular Part of the Growth Hormone Receptor in a Patient with Laron Syndrome" *J. Clin. Endocrino. and Metab.* 76:54–59 (1993).

Kowarski et al., "Growth Failure with Normal Serum RIA–GH and Low Somatomedin Activity: Somatomedin Restoration and Growth Acceleration After Exogenous GH" *J. Clin. Endocrinol. and Metab.* 47 (2) :461–464 (1978).

Laron et al., "Serum GH Binding Protein Activities Identifies the Heterozygous Carriers for Laron Type Dwarfism" *Acta Endocrinologica* 121 :603–608 (1989).

Martin et al., "Effects of Insulin–Like Growth Factor–I Peptides in Rats with Acute Renal Failure" *J. Endocrinol.* 140:23–32 (1994).

Martin et al., "IGF–I and its Variant, des–(1–3) IGF–I, Enhance Growth in Rats with Reduced Renal Mass" *Am. J. Physiol.* 261:F626–633 (1991).

Martin et al., "Insulin–Like Growth Factor I and its Variant, Des(1–3)IGF–I, Improve Nitrogen Balance and Food Utilization in Rats with Renal Failure" *Miner. Electrolyte Metab.* 18:264–268 (1992).

Mauras et al., "Growth Hormone–Binding Protein Levels: Studies of Children with Short Stature" *Metabolism* 43 (3) :357–359 (1994).

Pharmacia, "IGF–I: Wide–Ranging Benefits" *GH Insensitivity Syndromes*, England:Oxford Clinical Communications (Oct. 1993).

Read et al., "Insulin–Like Growth Factor–I and its N–terminal Modified Analogues Induce Marked Gut Growth in Dexamethasone–Treated Rats" *J. Endocrinol*, 133:421–431 (1992).

(List continued on next page.)

*Primary Examiner*—Howard E. Schain
*Assistant Examiner*—Lynn Touzeau
*Attorney, Agent, or Firm*—Janet E. Hasak

[57] ABSTRACT

Methods for increasing the growth rate of a human patient having partial growth hormone insensitivity syndrome, but not Laron syndrome, are described. One such method comprises administering a dose of greater than 0.3 mg/kg/week of growth hormone, preferably growth hormone with a native human sequence, with or without an N-terminal methionine, to the patient. The patient is characterized as having a height of less than about −2 standard deviations below normal for age and sex, serum levels of high-affinity growth hormone binding protein and IGF-I that are at least 2 standard deviations below normal levels, and a serum level of growth hormone that is at least normal. In another such method, the same patient population is treated with an effective amount of IGF-I alone or in combination with an amount of growth hormone that is effective in combination with IGF-I.

8 Claims, 8 Drawing Sheets

OTHER PUBLICATIONS

Rose et al., "The Advantage of Measuring Stimulated as Compared with Spontaneous Growth Hormone Levels in the Diagnosis of Growth Hormone Deficiency" *New England J. of Medicine* 319:201–207 (1988).

Rosenbloom et al., "Is There Heterozygote Expression of Growth Hormone Receptor Deficiency?" *Acta Paediatr. Suppl.* 399:125–127 (1994).

Rosenfeld et al.,"Growth Hormone (GH) Insensittivity Due to Primary GH Receptor Deficiency" *Endocrine Reviews* 15 (3) :369–390 (1994).

Tomas et al., "Anabolic Effects of Insulin–Like Growth Factor–I (IGF–I) and an IGF–I Variant in Normal Female Rats" *J. Endocrinol,* 137:413–421 (1993).

Tomas et al., "Insulin–Like Growth Factor–I and more Potent Variants Restore Growth of Diabetic Rats Without Inducing All Characteristic Insulin Effects" *Biochemistry* 291:781–786 (1993).

v. Kalckreuth, "Constitutional Delay of Growth and Puberty: Do They Really Reach Their Target Height?" *Horm. Res.* 35:222–225 (1991).

Valenta et al., "Pituitary Dwarfism in a Patient with Circulating Abnormal Growth Hormone Polymers" *New England J. of Medicine* 312:214–217 (1985).

Albertsson–Wikland, "Growth Hormone Treatment in Short Children–Short–Term and Long–Term Effects on Growth", *Acta Paediatr Scand (Suppl),* 343:77–84 (1988).

Albertsson–Wikland et al., "Analyses of 24–Hour Growth Hormone Profiles in Children: Relation to Growth", *Journal of Clinical Endocrinology and Metabolism,* 67(3):493–500 (1988).

Amselem et al., "Molecular Basis of Laron Dwarfism", *TEM—Elsevier Science Publishing Co., Inc.,* pp. 35–40, (1991).

Amselem et al., "Laron Dwarfism and Mutations of the Growth Hormone–Receptor Gene", *The New England Journal of Medicine,* 321(15):989–995 (1989).

Amselem et al., "Molecular Defects in the Growth Hormone Receptor", *Acta Paediatr Scand [Suppl],* 377:81–86 (1991).

Attie et al., "Evidence for Partial Growth Hormone (GH) Insensitivity among Idiopathic Short Stature (ISS) Patients Treated with growth Hormone", *4th Joint LWPES/ESPE Meeting San Francisco* (1993).

Backeijauw et al., "Effects of Prolonged IGF–I Treatment in Children with Growth Hormone Insensitivity Syndrome (GHIS)", *Pediatr. Res.,* 33:S56, 5 Suppl., #314 (1993).

Baumann et al., "Absence of the Plasma Growth Hormone–Binding Protein in Laron–Type Dwarfism", *Journal of Clinical Endocrionology and Metabolism,* 65(4):814–816 (1987).

Baumann et al., "Circulating Molecular Varients of Growth Hormone in Childhood", *Pediatric Research,* 22(1):21–22 (1987).

Baumann et al., "Short Stature and Decreased Serum Growth Hormone–Binding Protein in the Mountain Ok People of Papua New Guinea", *Journal of Clinical Endocrionology and Metabolism,* 72(6):1346–1349 (1991).

Baumbach et al., "The Growth Hormone–Binding Protein in Rat Serum is an Alternatively Spliced Form of the Rat Growth Hormone Receptor", *Genes & Development,* 3:1199–1205 (1989).

Bierich et al., "Die Spontansekretion des Wachstumshormons bei der konstittionellen Entwicklungsverzögerung und der froöhnormalen Pubertat", *Monatsschritt fur Kinderheilkunde,* 127:561–565 (1979).

Blum et al., "Growth Hormone Insensitivity Syndromes: A Preliminary Report On Charges in Insulin–Like Growth Factors and Their Binding Proteins During Treatment with Recombinant Insulin–Like Factor I", *Acta Paediatr Suppl,* 391:15–19 (1993).

Blum et al., "Clinical Studies of IGFBP–2 by Radioimmunoassay", *Growth Regulations,* 3:100–104 (1993).

Bramswig et al., "Adult Height in Boys and Girls with Untreated Short Stature and Constitutional Delay of Growth–And Puberty: Accuracy of Five Different Methods of Height Prediction", *The Journal of Pediatrics,* 117:886–891 (1990).

Buchanan et al., "Laron–Type Dwarfism with Apparently Normal High Affinity Serum Growth Hormone–Binding Protein", *Clinical Endocrinology,* 35:179–185 (1991).

Carlsson et al., "Analysis of 24–Hour Plasma Profiles of Growth Hormone (GH)–Binding Protein, GH/GH–Binding Protein–Complex, and GH in Healthy Children", *Journal of Clinical Endocrinology and Metabolism,.* 77(2):356–361 (1993).

Carlsson et al., "Decreased Growth Hormone (GH)–binding Protein and Normal Endogenous GH Secretion in Children with Idiopathic Short Stature", *The Amer. Pediatric Society/The Society for Pediatric Reasearch* (1992).

Carlsson et al., "Ligand–Mediated Immunofunctional Assay for Quantitation of Growth Hormone–Binding Protein in Human Blood", *Journal of Clinical Endocrinology and Metabolism,* 73(6):1216–1223 (1991).

Chan et al., "Expression of Insulin–Like Growth Factor–I in Uremic Rats: Growth Hormone Resistance and Nutritional Intake", *Kidney International,* 43:790–795 (1993).

Chanoine et al., "Growth Hormone (GH) Treatment in Short Normal Children: Absence of Influence of Time of Injection and Resistance to GH Autofeedback", *Journal of Clinical Endocrinology and Metabolism* 73(6):1269–1275 (1991).

Clemons et al., "Laron Dwarfism: Growth and Immunoreactive Insulin Following Treatment with Human Growth Hormone", *the Journal of Pediatrics,* 88(3):427–433 (1976).

Constantino et al., "Insulin–Resistant MDA–MB231 Human Breast Cancer Cells Contain a Tyrosine Kinase Inhibiting Activity", *Molecular Endocrinology,* 7(12):1667–1676.

Cotterill et al., "The Effect of Recombinant Human Insulin–Like Growth Factor–I Treatment on Growth Hormone Secretion in Two Subjects with Growth Hormone Insensitivity (Laron Syndrome)", *Clinical Endocrinology,* 39: 119–122 (1993).

Cowell et al., "Effects of Growth Hormone in Short, Slowly Growing Children Without Growth Hormone Deficiency", *Acta Paediatr Scand (Suppl)* 366:29–30 (1990).

Crowne et al., "Final Height in Boys with Untreated Constitutional Delay in Growth and Puberty", *Archives of Disease in Childhood* 65:1109–1112 (1990).

Cunningham et al., "Growth Hormone Binding Protein Enhances the Growth Promoting Activity of GH in the Rat", *The Endocrine Society—Program and Abstracts, 73rd Annual Meeting* 1611:433 (1991).

Daughaday et al., "Absence of Serum Growth Hormone Binding Protein in Patients with Growth Hormone Receptor Deficiency (Laron Dwarfism)", *Proc. Natl. Acad. Sci. USA* 84:4636–4640 (1987).

Diamond et al., "Hormonal, Metabolic and Pharmacokinetic Changes in Adults with Growth Hormone Receptor Deficiency Treated with Recombinant Human Insulin–Like Growth Factor I", *Acta Paediatr Suppl.* 383:148 (1992).

Fielder et al., "Serum Profiles of Insulin–Like Growth Factors and Their binding Proteins in Adults with Growth Hormone Receptor Deficiency Treated with Insulin–Like Growth Factor I", *Acta Paediatr Suppl,* 388:40–43 (1993).

Fielder et al., "Expression of Serum Insulin–Like Growth Factors, Insulin–Like Growth Factor–Binding Proteins, and the Growth Hormone–Binding Protein in Heterozygote Relatives of Equadorian Growth Hormone Receptor Deficient Patients", *Journal of Clinical Endocrinology and Metabolism* 74:743–750 (1992).

Fontoura et al., "Effects of growth hormone on the low level of growth hormone binding protein in idiopathic short stature", *Clinical Endocrinology* 37:249–253 (1992).

Frasier et al., "Clinical Review 11: The Rational Use of Growth Hormone During Childhood", *Journal of Clinical Endocrinology and Metabolism* 71:269–273 (1990).

Gargosky et al., "The Composition and Distribution of Insulin–Like Growth Factors (IGFs) and IGF–Binding Proteins (IGFBPs) in the Serum of Growth Hormone Receptor–Deficient Patients: Effects of IGFBP–I Therapy on IGF–3", *Journal of Clinical Endocrinology and Metabolism* 77:1683–1689 (1993).

Genentech, Inc., "Response to Growth Hormone in Children with Idiopathic Short Stature", *Acta Paediatr Scand (Suppl.)* 366:24–26 (1990).

Gluckman et al., "Therapeutic Use of Insulin–like Growth Factor I: Lessons From in vivo Animal Studies", *Acta Paediatr Suppl.* 383:134–136 (1992).

Gourmelan et al., "Effects of Exogenous Insulin–Like Growth Factor Binding Proteins in a Case of Growth Hormone Insensitivity (Laron–Type)", *Acta Paediatr Scand (Suppl)* 377:115–117 1991.

Grahnen et al., "Pharmacokinetics of Recombinant Human Insulin–like Growth Factor I Given Subcutaneously to Healthy Volunteers and to Patients with Growth Hormone Receptor Deficiency", *Acta Paediatr Suppl.* 391:9–13 (1993).

Grunt et al., "Growth, Short Stature, and the Use of Growth Hormone: Considerations for the Practicing Pediatrician", *Current Problems in Pediatrics* 22:390–412 (1992).

Guevara–Aquirre et al., "Growth Hormone Receptor Deficiency (Laron Syndrome): Clinical and Genetic Characteristics", *Acta Paediatr Scand (Suppl)* 377:96–103 (1991).

Hamill et all., "Physical Growth: National Center for Health Statistics percentiles", *The American Journal of Clinical Nutrition 32:* (special article), pp. 607–629 (1979).

Heinrichs et al., "Effects on 17 Months Treatment Using Recombinant Insulin–Like Growth Factor–I in Two Children with Growth Hormone Insensitivity (Laron) Syndrome", *Clinical Endocrinology* 38:647–651 (1993).

Hochberg et al., "Regulation of Growth Hormone Receptor Turnover by Growth Hormone", *Acta Paediatr Scand (Suppl)* 367:148–152 (1990).

Hopwood et al., "Growth response of children with non–growth–hormone deficiency and marked short stature during three years of growth hormone therapy", *The Journal of Pediatrics* 123:215–222 (1993).

Kalckreuth et al., "Constitutional Delay of Growth and Puberty: Do They Really Reach Their Target Height?", *Horm Res* 35:222–225 (1991).

Kanety et al., "Long–Term Treatment of Laron Type Dwarfs with Insulin–Like Growth Factor–1 Increases Serum Insulin–Like Growth Factor Binding Protein–3 in the Absence of Growth Hormone Activity", *Acta Endocrinologica* 128:144–149 (1993).

Kaplan et al., "Clinical Studies with Recombinant–DNA–Derived Methionyl Human Growth Hormone in Growth Hormone Deficient Children", *The Lancet* 1:697–700 (1986).

Kerrigan et al., "Altered–Growth Hormone Secretory Dynamics in Prepubertal Males with Constitutional Delay of Growth", *Pediatric Research* 33:278–283 (1993).

Kerrigan et al., "Variations of Pulsatile Growth Hormone Release in Healthy Short Prepubertal Boys", *Pediatric Research* 28:11–14 (1990).

LaFranchi et al., "Constitutional Delay of Growth: Expected versus Final Adult Height", *Pediatrics–Articles* 87:82–87 (1991).

Lanes, "Diagnostic Limitations of Spontaneous Growth Hormone Measurments in Normally Growing Prepubertal Children", *AJDC* 143:1284–1286 (1989).

Laron, "An Update on Laron Syndrome", *Archives of Disease in Childhood* 68:345–346 (1993).

Laron et al., "Biochemical and Hormontal Changes Induced by One Week of Administration of rIGF–I to Patients with Laron Type Dwarfism", *Clinical Endocrinology* 35:145–150 (1991).

Laron et al., "Body Fat in Laron Syndrome Patients: Effect of Insulin–Like Growth Factor I Treatment", *Horm Res* 40:16–22 (1993).

Laron et al., "Classification of Growth Hormone Insensitivity Syndrome", *The Journal of Pediatrics* 122(2):241.

Laron, "Disorders of Growth Hormone Resistance in Childhood", *Endocrine and metabolism, Current Science ISBN 1–85922–016–9 ISSN 1040–8703,* Children's Medical Center of Israel, and Sackler School of Medicine Tel Aviv, pp. 474–480 (1993).

Laron et al., "Effect of Acute Administration of Insulin–Like Growth Factor I in Patients with Laron–Type Dwarfism", *The Lancet* 2:1170–1172 (1988).

Laron et al., "Effects of Insulin–Like Growth Factor on Linear Growth, Head Circumference, and Body Fat in Patients with Laron–Type Dwarfism", *The Lancet,* vol. 339:1258–1260 (1992).

Laron, "GH Insensitivity Syndromes", *Int'l Workshop, Amsterdam Oxford Clinical Communications* pp. 1–4 (1992).

Laron et al., "Growth curves for Laron syndrome", *Archives of Disease in Childhood* 68:768–770 (1993).

Laron et al., "Laron Syndrome Due to a Post–Receptor Deffect: Response to IGF–I Treatment", *Israel Journal of Medical Sciences* 29:757–763 (1993).

Laron, "Laron Syndrome: From Description to Therapy", *The Endocrinologist* 3:22–28 (1993).

Laron et al. "Pediatric and Adolescent Endocrinology", 24:1–367, (1992).

Leonard et al., "Anthropometric Assessment of Anabolic and Lipolytic Effects of Recombinant IGF–I Therapy in 3 Children with Growth Hormone Insensitivity Syndrome (GHIS)", *Pediatr. Res.* 33:S43 (1993).

LeRoith et al., "Insulin–like Growth Factors in Health and Disease", *Annals of Internal Medicine* 116:854–862 (1992).

Leung et al., "Growth Hormone Receptor and Serum Binding Protein: Purification, Cloning and Expression", *Nature* 330:537–543 (1987).

Lim et al., "Regulation of Growth Hormone (GH) Bioactivity by a Recombinant Human GH–Binding Protein", *The Endocrine Society* 127:1287–1291 (1990).

Lippe et al., "Conventional and Nonconventional Uses of Growth Hormone", *Recent Progress in Hormone Research* 48:179–235 (1993).

Maddux et al., "Inhibitors of Insulin Receptor Tyrosine Kinase in Fibroblasts from Diverse Patients with Impaired Insulin Action: Evidence for a Novel Mechanism of Postreceptor Insulin Resistance", *Journal of Clinical Endocrinology and Metabolism,* 77:73–79 (1993).

Martha, Jr. et al., "Serum Growth Hormone (GH)–Binding Protein/Receptor: An Important Determinant of GH Responsiveness", *Journal of Clinical Endocrinology and Metabolism,* 75:1464–1469 (1992).

Martha et al., "Growth Hormone–Binding Protein Activity Is Inversely Related to 24–Hour Growth Hormone Release in Normal Boys", *Journal of Clinical Endocrinology and Metabolism* 73:175–181 (1991).

Martha et al., "Short Term Metabolic Changes and Long Term Response to Recombinant IGF–I (rhIGF–I) Therapy in a North American Child with GH Insensitivity (GHIS; Laron Syndrome)" *Pediatr. Res.* 33:S49 (1993).

Merimee et al., "Growth hormone–binding Protein: II. Studies in Pygmies and Normal Statured Subjects", *Journal of Clinical Endocrinology and Metabolism* 71:1183–1188 (1990).

Merimee et al., "Hormone and Receptor Studies: Relationship to Linear Growth in Childhood and Puberty", *Journal of Clinical Endocrinology and Metabolism* 73:1031–1037 (1991).

Momoi et al., "Short Stature with Normal Growth Hormone and Elevated IGF–"I, *Euro. Journal Pediatrics* 151:321–325 (1992).

Pierson et al., "Le Nanisme Familial De Type Laron, Deficit Genetique Primaire En Somatomedine", *Arch. Franc. Ped.,* 35:151–164 (1978).

Postel–Vinay et al., "Human Plasma Growth Hormone (GH)–Binding Proteins Are Regulated by GH and Testosterone", *Journal of Clinical Endocrinology and Metabolism* 73:197–201 (1991).

Preece, "Discussion—Could You Elaborate on the Management of the Four Patients with Severe Hypoglycaermia?", *Acta Paediatr Suppl.* 391:21 (1993).

Ranke et al., "Adult Height in Children with Constitutional Short Stature", *Acta Paediatr Scand Suppl.* 362:27–31 (1989).

Rogers–Rose et al., "The Advantage of Measuring Stimulated as Compared with Spontaneous Gowrth Hormone Levels in the Diagnosis of Growth Hormone Deficiency", *Developmental Endocrinology Branch Nat'l Inst. of Child Health snd Human Dev.* 319:201–207 (1988).

Rosenbloom, "The Chronicle of Growth Hormone Receptor Deficiency (Laron syndrome)", *Actapaediatr Suppl.* 383:117–120 (1992).

Santiago, "Lessons From the Diabetes Control and Complications Trial", *Diabetes* 42:1549–1554 (1993).

Savage et al. "Clinical Features and Endocrine Status in Patients with Growth Hormone Insensitivity (Laron Syndrome)", *Journal of Clinical Endocrinology and Metabolism* vol. 77, No. 6, pp. 1465–1471.

Savage et al. "Clinical Spectrum of the Syndrome of Growth Hormone Insensitivity", *Acta Paediatr Scand (Suppl)* 377:87–90 (1991).

Savage et al., "Therapeutic Response to Recombinant IGF–1 in Thirty Two Patients with Growth Hormone Insensitivity", *Pediatr. Res.* 33;S5 (1993).

Sbraccia et al., "Production of Inhibitor of Insulin–Receptor Tyrosine Kinase in Fibroblasts From Patient With Insulin Resistance and NIDDM", *Diabetes.* vol. 40, Feb. 1991.

Shafrir, "Genetic Dwarfism with High Growth Hormone Levels–Multiple Causation of GH Nonresponsiveness", *Israel Journal of Medical Sciences* 29:800–801 (1993).

Smith et al., "Mouse Serum Growth Hormone (GH) Binding Protein has GH Receptor Extracellular and Substituted Transmemebrane Domains", *Molecular Endocrinology* 3:984–990 (1989).

Spiliotis et al., "Growth Hormone Neurosecretory Dysfunction", *The Journal of the American Medical Assn.* 251:2223–2230.

Takano et al., "Effects of Short–Term Growth Hormone Thearpy in Short Children without Growth Hormone Deficiency", *Acta Paediatr Scand (Suppl)* 366:14–22 (1990).

Tönshoff. et al., "Effects of Two Years of Growth Hormone Treatment in Short children with Renal Disease", *Acta Paediatr Scand [Suppl]* 379:33–41 (1991).

Trivedi et al., "Release of Growth Hormone Binding Protein from IM–9 Lymphocytes by Endopeptidase is Dependent on Sulfydryl Group Inactivation", *The Endocrine Society* 123:2201–2206 (1988).

Underwood et al., "IGFs: Function and Clinical Importance 6 Therapy with Recombinant Human Insulin–like Growth Factor I in Children with Insensitivity to Growth Hormone and in Catabolic Conditions", *Journal of Internal Medicine* 234:571–577 (1993).

Vaccarello et al., "Hormonal and Metabolic Effects and Pharmacokinetics of Recombinant Insulin–Like Growth Factor–I in Growth Hormone Receptor Deficiency/Laron Syndrome", *Journal of Clinical Endocrinology and Metabolism* 77:273–280 (1993).

Veldhuis et al., "Properties of Spontaneous Growth Hormone Secretory Bursts and Half–Life of Endogenous Growth Hormone in Boys with Idiopathic Short Stature", *Journal of Clinical Endocrinology and Metabolism* 74:766–773 (1992).

Walker et al., "Effects of the Infusion of Insulin–Like Growth Factor I in a Child with Growth Hormone Insensitivity Syndrome (Laron Dwarfism)", *Brief Report* 324:1483–1488 (1991).

Walker et al., "Effects of Recombinant Insulin–Like Growth Factor I on IGF Binding Proteins and the Acid–Labile Subunit in Growth Hormone Insensitivity Syndrome ", *Growth Regulation* pp.109–112.

Walker et al., "Stimulation of Statural Growth by Recombinant Insulin–Like Growth Factor I in a Child with Growth Hormone Insensitivity Syndrome (Laron Type)", *The Journal of Pediatrics* 121:641–646 (1992).

Wilton et al., "Treatment with Recombinant Human Insulin–Like Growth Factor I of Children with Growth Hormone Receptor Deficiency (LaronSsyndrome)", *Acta Paediatr Supp.l* 383:137–41 (1992).

Zadik et al., "Do Short Children Secrete Insufficient Growth Hormone?", *Pediatrics—Articles* 76:355–360 (1985).

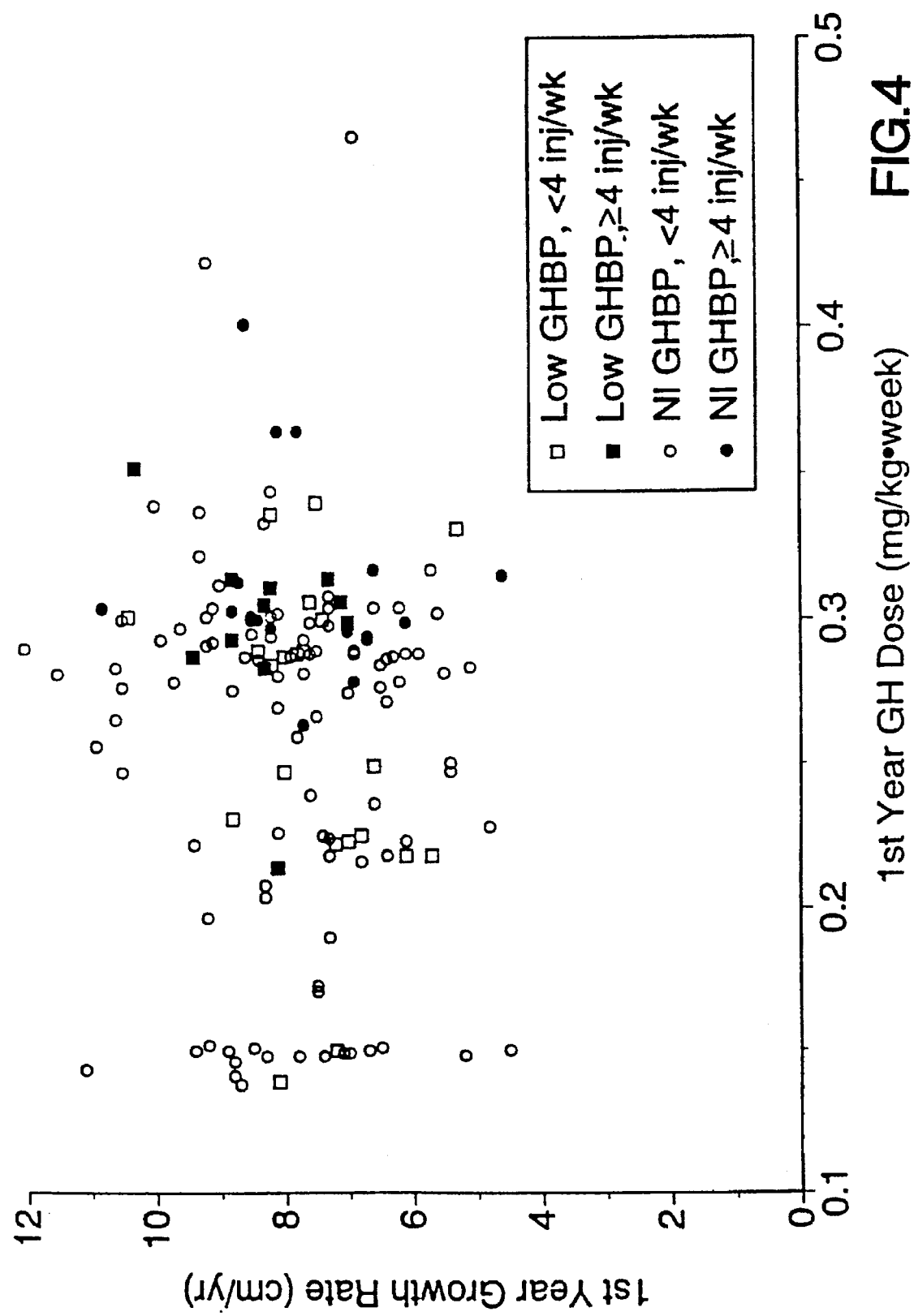

```
GHR allele 1  ATCCTCTAAG GAGCCTAAAT TCACCAAGTG CCGTTCACCT GAGCGAGAGA CTTTTTCATG CCACTGGACA
              S  S  K     E  P  K  F    T  K  C      R  S  P       E  R  E  T    F  S  C     H  W  T
GHR allele 2  ATCCTCTAAG GAGCCTAAAT TCACCAAGTG CCGTTCACCT GAGCGAAAGA CTTTTTCATG CCACTGGACA
              S  S  K     E  P  K  F    T  K  C      R  S  P       E  R  K  T    F  S  C     H  W  T GHR allele 1  GATGAGGTTC ATCATGGTAC AAAGAACCTA GGACCCATAC AGCTGTTCTA TACCAGAAG|G AACACTCAAG
              D  E  V  H   H  G  T    K  N  L       G  P  I  Q      L  F  Y     T  R  R      N  T  Q  E
GHR allele 2  GATGAGGTTC ATCATGGTAC AAAGAACCTA GGACCCATAC AGCTGTTCTA TACCAGAAG|G AACACTCAAG
              D  E  V  H   H  G  T    K  N  L       G  P  I  Q      L  F  Y     T  R  R      N  T  Q  E GHR allele 1  AATGGACTCA AGAATGGAAA GAATGCCCTG ATTATGTTTC TGCTGGGGAA AACAGCTGTT ACTTTAATTC
              W  T  Q     E  W  K     N  L  E        E  C  P  D       Y  V  S     A  G  E      N  S  C  Y  F  N  S
GHR allele 2  AATGGACTCA AGAATGGAAA GAATGCCCTG ATTATGTTTC TGCTGGGGAA AACAGCTGTT ACTTTAATTC
              W  T  Q     E  W  K     N  L  E        E  C  P  D       Y  V  S     A  G  E      N  S  C  Y  F  N  S GHR allele 1  ATCGTTTACC TCCATCTGGA TACCTTATTG TATCAAGCTA ACTAGCAATG GTGGTACAGT GGATGAAAAG
              S  F  T     S  I  W     I  P  Y  C     I  K  L         T  S  N  G     G  T  V     D  E  K
GHR allele 2  ATCGTTTACC TCCATCTGGA TACCTTATTG TATCAAGCTA ACTAGCAATG GTGGTACAGT GGATGAAAAG
              S  F  T     S  I  W     I  P  Y  C     I  K  L         T  S  N  G     G  T  V     D  E  K GHR allele 1  TGTTTCTCTG TTGATGAAAT AG|TGCAACCA GATCCACCCA TTGCCCTCAA CTGGACTTTA CTGAACGTCA
              C  F  S  V    D  E  I    Q|Q  P         D  P  P  I     A  L  N       W  T  L       N  V  S
GHR allele 2  TGTTTCTCTG TTGATGAAAT AG|TGCAACCA GATCCACCCA TTGCCCTCAA CTGGACTTTA CTGAACGTCA
              C  F  S  V    D  E  I    Q|Q  P         D  P  P  I     A  L  N       W  T  L       N  V  S GHR allele 1  GTTTAACTGG GATTCATGCA GATATCCAAG TGAGATGGGA AGCACCAGC AATGCAGATA TTCAGAAAGG
              L  T  G     I  H  A     D  I  Q  V      R  W  E        A  P  C       N  A  D  I    Q  K  G
GHR allele 2  GTTTAACTGG GATTCATGCA GATATCCAAG TGAGATGGGA AGCACCACGC AATGCAGATA TTCAGAAAGG
              L  T  G     I  H  A     D  I  Q  V      R  W  E        A  P  R       N  A  D  I    Q  K  G GHR allele 1  GTGGATGGTT CTGGAGTATG AACTT
              W  M  V     L  E  Y  E    L
GHR allele 2  GTGGATGGTT CTGGAGTATG AACTT
              W  M  V     L  E  Y  E    L
```

FIG.6

```
GHR allele 1    GAACACTCAA GAATGGACTC AAGAATGGAA AGAATGCCCT GATTATGTTT CTGCTGGGGA
                 N  T  Q    E  W  T  Q   E  W  K     E  C  P     D  Y  V  F    L  L  G  E GHR allele 2    GAACACTCAA GAATGGACTC AAGAATGGAA AGAATGCCCT GATTATGTTT CTGCTGGGGA
                 N  T  Q    E  W  T  Q   E  W  K     E  C  P     D  Y  V  F    L  L  G  E GHR allele 1    AAACAGCTGT TACTTTAATT CATCGTTTAC CTCCATCTGG ATACCTTATT GTATCAAGCT
                 N  S  C    Y  F  N  S   S  F  T     S  I  W    I  P  Y  C    I  K  L GHR allele 2    AAACAGCTGT TACTTTAATT CATCGTTTAC CTCCATCTGG ATACCTTATT GTATCAAGCT
                 N  S  C    Y  F  N  S   S  F  T     S  I  W    I  P  Y  C    I  K  L GHR allele 1    AACTAGCAAT GGTGGTACAG TGGATGAAAA GTGTTTCTCT GTTGATGAAA TAG
                 T  S  N    G  G  T  V   D  E  K     C  F  S     V  D  E  I GHR allele 2    AACTAGCAAT GGTGGTACAG TGGATGAAAA GTGATTCTCT GTTGATGAAA TAG
                 T  S  N    G  G  T  V   D  E  K    Stop
```

FIG. 7

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 445 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ATCCTCTAAG  GAGCCTAAAT  TCACCAAGTG  CCGTTCACCT  GAGCGAGAGA    50

CTTTTTCATG  CCACTGGACA  GATGAGGTTC  ATCATGGTAC  AAAGAACCTA   100

GGACCCATAC  AGCTGTTCTA  TACCAGAAGG  AACACTCAAG  AATGGACTCA   150

AGAATGGAAA  GAATGCCCTG  ATTATGTTTC  TGCTGGGGAA  AACAGCTGTT   200

ACTTAATTC   ATCGTTTACC  TCCATCTGGA  TACCTTATTG  TATCAAGCTA   250

ACTAGCAATG  GTGGTACAGT  GGATGAAAAG  TGTTTCTCTG  TTGATGAAAT   300
```

```
AGTGCAACCA  GATCCACCCA  TTGCCCTCAA  CTGGACTTTA  CTGAACGTCA  350

GTTTAACTGG  GATTCATGCA  GATATCCAAG  TGAGATGGGA  AGCACCATGC  400

AATGCAGATA  TTCAGAAAGG  GTGGATGGTT  CTGGAGTATG  AACTT       445
```

( 2 ) INFORMATION FOR SEQ ID NO:2:

( i ) SEQUENCE CHARACTERISTICS:
        ( A ) LENGTH: 445 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
ATCCTCTAAG  GAGCCTAAAT  TCACCAAGTG  CCGTTCACCT  GAGCGAAAGA  50

CTTTTTCATG  CCACTGGACA  GATGAGGTTC  ATCATGGTAC  AAAGAACCTA  100

GGACCCATAC  AGCTGTTCTA  TACCAGAAGG  AACACTCAAG  AATGGACTCA  150

AGAATGGAAA  GAATGCCCTG  ATTATGTTTC  TGCTGGGGAA  ACAGCTGTT   200

ACTTTAATTC  ATCGTTTACC  TCCATCTGGA  TACCTTATTG  TATCAAGCTA  250

ACTAGCAATG  GTGGTACAGT  GGATGAAAAG  TGTTTCTCTG  TTGATGAAAT  300

AGTGCAACCA  GATCCACCCA  TTGCCCTCAA  CTGGACTTTA  CTGAACGTCA  350

GTTTAACTGG  GATTCATGCA  GATATCCAAG  TGAGATGGGA  AGCACCACGC  400

AATGCAGATA  TTCAGAAAGG  GTGGATGGTT  CTGGAGTATG  AACTT       445
```

( 2 ) INFORMATION FOR SEQ ID NO:3:

( i ) SEQUENCE CHARACTERISTICS:
        ( A ) LENGTH: 148 amino acids
        ( B ) TYPE: amino acid
        ( D ) TOPOLOGY: linear ( x i ) SEQUENCE DESCRIPTION: SEQ ID NO:3:

```
Ser  Ser  Lys  Glu  Pro  Lys  Phe  Thr  Lys  Cys  Arg  Ser  Pro  Glu  Arg
 1              5                        10                         15

Glu  Thr  Phe  Ser  Cys  His  Trp  Thr  Asp  Glu  Val  His  His  Gly  Thr
               20                        25                         30

Lys  Asn  Leu  Gly  Pro  Ile  Gln  Leu  Phe  Tyr  Thr  Arg  Arg  Asn  Thr
               35                        40                         45

Gln  Glu  Trp  Thr  Gln  Glu  Trp  Lys  Glu  Cys  Pro  Asp  Tyr  Val  Ser
               50                        55                         60

Ala  Gly  Glu  Asn  Ser  Cys  Tyr  Phe  Asn  Ser  Ser  Phe  Thr  Ser  Ile
               65                        70                         75

Trp  Ile  Pro  Tyr  Cys  Ile  Lys  Leu  Thr  Ser  Asn  Gly  Gly  Thr  Val
               80                        85                         90

Asp  Glu  Lys  Cys  Phe  Ser  Val  Asp  Glu  Ile  Val  Gln  Pro  Asp  Pro
               95                       100                        105

Pro  Ile  Ala  Leu  Asn  Trp  Thr  Leu  Leu  Asn  Val  Ser  Leu  Thr  Gly
              110                       115                        120

Ile  His  Ala  Asp  Ile  Gln  Val  Arg  Trp  Glu  Ala  Pro  Cys  Asn  Ala
              125                       130                        135

Asp  Ile  Gln  Lys  Gly  Trp  Met  Val  Leu  Glu  Tyr  Glu  Leu
              140                       145           148
```

( 2 ) INFORMATION FOR SEQ ID NO:4:

( i ) SEQUENCE CHARACTERISTICS:

(A) LENGTH: 148 amino acids
(B) TYPE: amino acid
(D) TOPOLOGY: linear (xi) SEQUENCE DESCRIPTION: SEQ ID NO:4:

```
Ser Ser Lys Glu Pro Lys Phe Thr Lys Cys Arg Ser Pro Glu Arg
 1               5                  10                  15

Lys Thr Phe Ser Cys His Trp Thr Asp Glu Val His His Gly Thr
                20                  25                  30

Lys Asn Leu Gly Pro Ile Gln Leu Phe Tyr Thr Arg Arg Asn Thr
                35                  40                  45

Gln Glu Trp Thr Gln Glu Trp Lys Glu Cys Pro Asp Tyr Val Ser
                50                  55                  60

Ala Gly Glu Asn Ser Cys Tyr Phe Asn Ser Ser Phe Thr Ser Ile
                65                  70                  75

Trp Ile Pro Tyr Cys Ile Lys Leu Thr Ser Asn Gly Gly Thr Val
                80                  85                  90

Asp Glu Lys Cys Phe Ser Val Asp Glu Ile Val Gln Pro Asp Pro
                95                 100                 105

Pro Ile Ala Leu Asn Trp Thr Leu Leu Asn Val Ser Leu Thr Gly
               110                 115                 120

Ile His Ala Asp Ile Gln Val Arg Trp Glu Ala Pro Arg Asn Ala
               125                 130                 135

Asp Ile Gln Lys Gly Trp Met Val Leu Glu Tyr Glu Leu
               140                 145         148
```

(2) INFORMATION FOR SEQ ID NO:5:

(i) SEQUENCE CHARACTERISTICS:
(A) LENGTH: 173 bases
(B) TYPE: nucleic acid
(C) STRANDEDNESS: single
(D) TOPOLOGY: linear (xi) SEQUENCE DESCRIPTION: SEQ ID NO:5:

```
GAACACTCAA GAATGGACTC AAGAATGGAA AGAATGCCCT GATTATGTTT    50
CTGCTGGGGA AAACAGCTGT TACTTTAATT CATCGTTTAC CTCCATCTGG   100
ATACCTTATT GTATCAAGCT AACTAGCAAT GGTGGTACAG TGGATGAAAA   150
GTGTTTCTCT GTTGATGAAA TAG                                173
```

(2) INFORMATION FOR SEQ ID NO:6:

(i) SEQUENCE CHARACTERISTICS:
(A) LENGTH: 173 bases
(B) TYPE: nucleic acid
(C) STRANDEDNESS: single
(D) TOPOLOGY: linear (xi) SEQUENCE DESCRIPTION: SEQ ID NO:6:

```
GAACACTCAA GAATGGACTC AAGAATGGAA AGAATGCCCT GATTATGTTT    50
CTGCTGGGGA AAACAGCTGT TACTTTAATT CATCGTTTAC CTCCATCTGG   100
ATACCTTATT GTATCAAGCT AACTAGCAAT GGTGGTACAG TGGATGAAAA   150
GTGATTCTCT GTTGATGAAA TAG                                173
```

(2) INFORMATION FOR SEQ ID NO:7:

(i) SEQUENCE CHARACTERISTICS:
(A) LENGTH: 57 amino acids
(B) TYPE: amino acid ( D ) TOPOLOGY: linear ( x i ) SEQUENCE DESCRIPTION: SEQ ID NO:7:

| Asn | Thr | Gln | Glu | Trp | Thr | Gln | Glu | Trp | Lys | Glu | Cys | Pro | Asp | Tyr |
|-----|-----|-----|-----|-----|-----|-----|-----|-----|-----|-----|-----|-----|-----|-----|
| 1 | | | | 5 | | | | | 10 | | | | | 15 |
| Val | Ser | Ala | Gly | Glu | Asn | Ser | Cys | Tyr | Phe | Asn | Ser | Ser | Phe | Thr |
| | | | | 20 | | | | | 25 | | | | | 30 |
| Ser | Ile | Trp | Ile | Pro | Tyr | Cys | Ile | Lys | Leu | Thr | Ser | Asn | Gly | Gly |
| | | | | 35 | | | | | 40 | | | | | 45 |
| Thr | Val | Asp | Glu | Lys | Cys | Phe | Ser | Val | Asp | Glu | Ile | | | |
| | | | | 50 | | | | | 55 | | 57 | | | |

( 2 ) INFORMATION FOR SEQ ID NO:8:

( i ) SEQUENCE CHARACTERISTICS:
  ( A ) LENGTH: 50 amino acids
  ( B ) TYPE: amino acid
  ( D ) TOPOLOGY: linear ( x i ) SEQUENCE DESCRIPTION: SEQ ID NO:8:

| Asn | Thr | Gln | Glu | Trp | Thr | Gln | Glu | Trp | Lys | Glu | Cys | Pro | Asp | Tyr |
|-----|-----|-----|-----|-----|-----|-----|-----|-----|-----|-----|-----|-----|-----|-----|
| 1 | | | | 5 | | | | | 10 | | | | | 15 |
| Val | Ser | Ala | Gly | Glu | Asn | Ser | Cys | Tyr | Phe | Asn | Ser | Ser | Phe | Thr |
| | | | | 20 | | | | | 25 | | | | | 30 |
| Ser | Ile | Trp | Ile | Pro | Tyr | Cys | Ile | Lys | Leu | Thr | Ser | Asn | Gly | Gly |
| | | | | 35 | | | | | 40 | | | | | 45 |
| Thr | Val | Asp | Glu | Lys | | | | | | | | | | |
| | | | | 50 | | | | | | | | | | |

TREATMENT OF PARTIAL GROWTH HORMONE INSENSITIVITY SYNDROME

BACKGROUND OF THE INVENTION

1. Field of the Invention

This invention relates to a method for increasing the growth rates of human patients having partial growth hormone insensitivity syndrome.

2. Description of Background and Related Art

Most children who are evaluated for short stature do not have growth hormone deficiency as defined by the growth hormone (GH) response to provocative stimuli. Once other causes of short stature have been excluded, the patient is usually classified as having familial short stature, constitutional delay of growth, or "idiopathic" short stature (ISS). Despite not being classically GH deficient, most children with ISS respond to treatment with GH, although not as well. Since there are so many factors that contribute to normal growth and development, it is likely that this group of patients is heterogeneous with regard to their etiology of short stature.

Many investigators have searched for disturbances in spontaneous GH secretion in this set of patients. One hypothesis suggests that some of these patients have inadequate secretion of endogenous GH under physiologic conditions, but are able to demonstrate a rise in GH in response to pharmacologic stimuli, as in traditional GH stimulation tests. This disorder has been termed "GH neurosecretory dysfunction," and the diagnosis rests on the demonstration of an abnormal GH pattern on prolonged serum sampling. Numerous investigators have reported results of such studies, and have found this abnormality to be only occasionally present. Other investigators have postulated that these patients have "bioinactive GH;" however, this has not yet been demonstrated.

When the GH receptor was cloned, it was shown that the major GH binding activity in blood was due to a protein which derives from the same gene as the GH receptor and corresponds to the extracellular domain of the full-length GH receptor. Most patients with growth hormone insensitivity (or Laron) syndrome (GHIS) lack growth hormone receptor binding activity and have absent or very low GH-binding protein (GHBP) activity in blood. Such patients have a mean height standard deviation score of about −5 to −6, are resistant to GH treatment, and have increased serum concentrations of GH and low serum concentrations of insulin-like growth factor (IGF-I). They respond to treatment with IGF-I. In patients with defects in the extracellular domain of the GH receptor, the lack of functional GHBP in the circulation can serve as a marker for the GH insensitivity.

There is a subclass of patients with ISS having low GHBP in their blood who have a mean height standard deviation score intermediate between patients with complete GHIS (Laron syndrome) and normal children, and who respond somewhat, but not completely, to GH treatment. This class of patients can be characterized as having partial GHIS.

It is an object of the present invention to identify a subset of patients with ISS who exhibit partial GHIS and do not have complete GHIS or Laron syndrome.

It is another object to treat this identified subset of patients so that they attain ultimate height consistent with their genetic potential as determined by the mid-parental target height.

These and other objects will be apparent to those of ordinary skill in the art.

SUMMARY OF THE INVENTION

Accordingly, in one aspect, the present invention provides a method for increasing the growth rate of a human patient having partial GHIS comprising administering a dose of greater than 0.3 mg/kg/week of GH to said patient, whereby said patient has a height less than about −2 standard deviations below normal for age and sex, and has serum levels of high-affinity GHBP and IGF-I that are at least 2 standard deviations below normal levels and has a mean or maximum stimulated serum level of GH that is at least normal, wherein the patient does not have Laron syndrome.

In another aspect, the invention provides a method for increasing the growth rate of a human patient having partial GHIS comprising administering an effective amount of IGF-I (preferably human recombinant IGF-I) to said patient, whereby said patient has a height less than about −2 standard deviations below normal for age and sex, and has serum levels of high-affinity GHBP and IGF-I that are at least 2 standard deviations below normal levels and has a mean or maximum stimulated serum level of GH that is at least normal, wherein the patient does not have Laron syndrome.

In a further aspect, the invention supplies a method for increasing the growth rate of a human patient having partial growth hormone insensitivity syndrome comprising administering amounts of IGF-I and growth hormone to said patient which amounts are effective in combination, whereby said patient has a height less than about −2 standard deviations below normal for age and sex, and has serum levels of high-affinity growth hormone binding protein and IGF-I that are at least 2 standard deviations below normal levels and has a mean or maximum stimulated serum level of growth hormone that is at least normal, wherein the patient does not have Laron syndrome, as defined herein.

BRIEF DESCRIPTION OF THE DRAWINGS

FIG. 4 depicts the first-year annualized growth rate (cm/yr) by weighted average dose of GH (mg/kg.week). Closed symbols represent patients treated with ≧4 injections/week and open symbols represent patients treated with <4 injections/week. Patients with low GHBP levels (SDS≧−2, squares) are differentiated from patients with normal GHBP levels (SDS>−2, circles).

FIG. 6 shows the DNA sequences (SEQ ID NOS 1 and 2, respectively) and predicted amino acid sequences (SEQ ID NOS 3 and 4, respectively) of two GH receptor (GHR) alleles in ISS Patient 4 (exons 4–6). The mutations in alleles 1 and 2 are indicated in bold type. The vertical bars indicate exon boundaries in the cDNA sequence.

FIG. 7 shows the DNA sequences (SEQ ID NOS 5 and 6, respectively) and predicted amino acid sequences (SEQ ID NOS 7 and 8, respectively) of two GHR alleles in ISS Patient 2 (exon 5). The mutations in allele 2 are indicated in bold type.

DESCRIPTION OF THE PREFERRED EMBODIMENTS

Figure 1A:
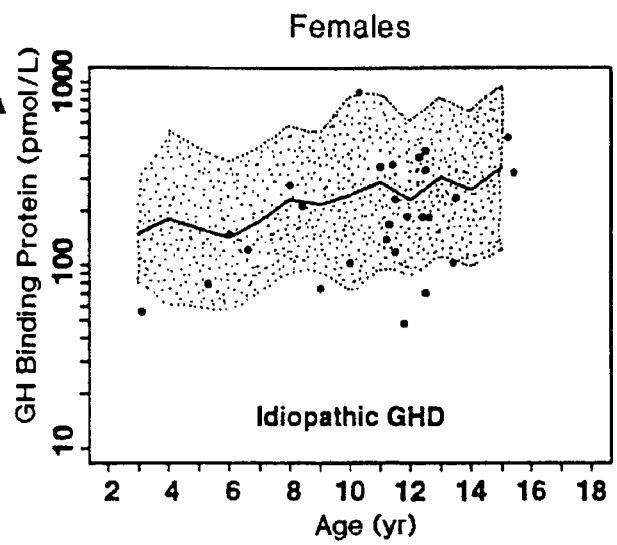
FIGS. 1A–1E show serum GHBP concentrations in children with growth hormone deficiency (GHD), idiopathic short stature (ISS), and Turner syndrome (TS) standardized for age and sex and expressed as standard deviation (SD) score, by age at the time of enrollment in the study. The shaded area represents the normal range (−2 SD to +2 SD) for each sex. The solid line indicates the normal mean for age and sex. Occasionally, points for two or more patients overlap and appear as a single point.
Figure 1B:
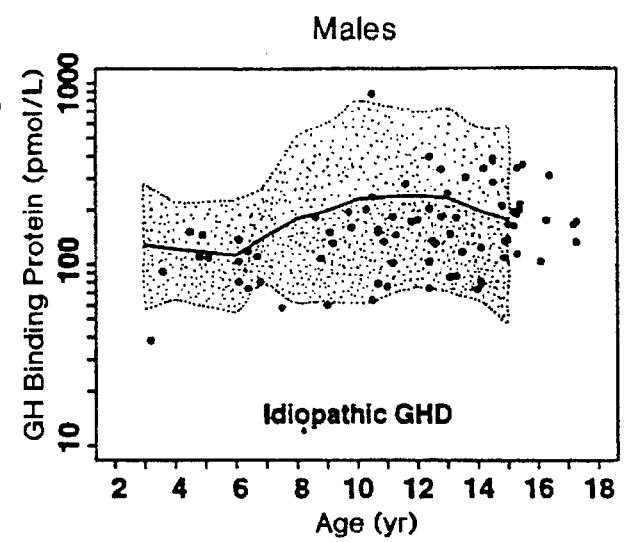
Figure 1C:
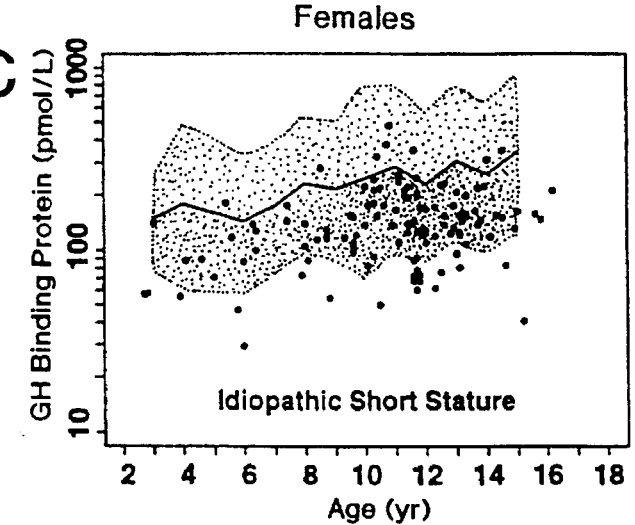
Figure 1D:
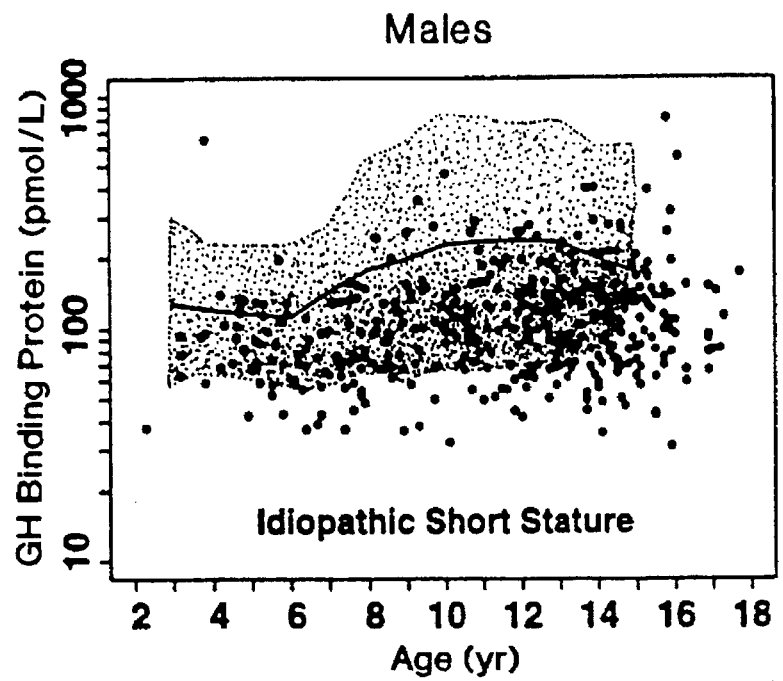
Figure 1E:
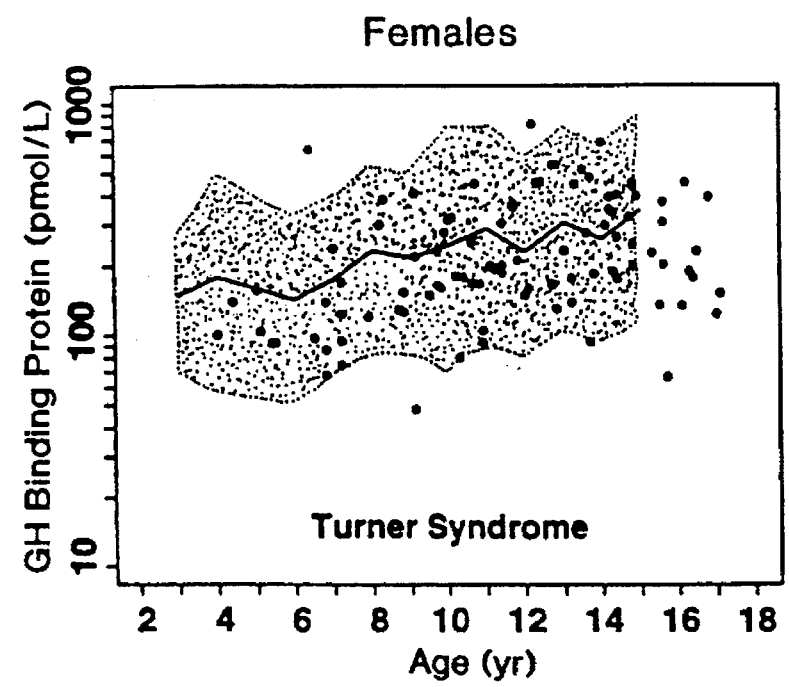

Definitions:

The patient population treated by the method of this invention excludes patients with "Laron syndrome," otherwise known and defined herein as people with complete growth hormone receptor lack of function or complete GHIS. These patients attain an adult height of only 110–130 cm. Additional common symptoms include slow growth, small face and jaw, depressed nasal bridge, frontal bossing, obesity, high-pitched voice, and hypoglycemia in early childhood. Biochemically, they are characterized by having increased serum concentrations of GH but low serum concentrations of IGF-I.

"Increasing the growth rate of a human patient" includes not only the situation where the patient attains at least the same ultimate height as GH-deficient patients treated with GH, but also refers to a situation where the patient catches up in height at the same growth rate as GH-deficient patients treated with GH, or achieves adult height that is within the target height range, i.e., an ultimate height consistent with their genetic potential as determined by the mid-parental target height.

"Partial growth hormone insensitivity syndrome" or "partial GHIS" refers to a syndrome wherein the patient responds to the same doses of GH as that given to GH-deficient patients, but does not respond as well. This syndrome is further characterized in that the patient has a height of less than about −2 standard deviations below normal for age and sex, preferably in the range of less than about −2 to about −4 standard deviations below normal for age and sex, has serum levels of high-affinity GHBP and IGF-I that are at least 2 standard deviations (typically 2–4 standard deviations) below normal levels for humans, and has a mean or maximum stimulated serum level of GH that is at least normal for humans. Mean serum levels are the mean of measurements in the patient.

As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or variant produced by means of recombinant DNA technology, including somatrem, somatotropin, and somatropin. Preferred herein for human use is recombinant human native-sequence, mature GH with or without a methionine at its N-terminus. More preferred is methionyl human growth hormone (met-hGH) produced in E. coli, e.g., by the process described in U.S. Pat. No. 4,755,465 issued Jul. 5, 1988 and Goeddel et al., Nature, 282: 544 (1979). Met-hGH, which is sold under the trademark Protropin® by Genentech, Inc., is identical to the natural polypeptide, with the exception of the presence of an N-terminal methionine residue. This added amino acid is a result of the bacterial protein synthesis process. Also preferred is recombinant hGH available from Genentech, Inc. under the trademark Nutropin®. This latter hGH lacks this methionine residue and has an amino acid sequence identical to that of the natural hormone. See Gray et al., Biotechnology, 2: 161 (1984). Both methionyl hGH and hGH have equivalent potencies and pharmacokinetic values. Moore et al., Endocrinology, 122: 2920–2926 (1988). Another appropriate hGH candidate is an hGH variant that is a placental form of GH with pure somatogenic and no lactogenic activity as described in U.S. Pat. No. 4,670,393 issued 2 Jun. 1987. Also included are GH variants as described in WO 90/04788 published 3 May 1990 and WO 92/09690 published 11 Jun. 1992.

As used herein, "IGF-I" refers to insulin-like growth factor-I from any species, including bovine, ovine, porcine, equine, arian, and preferably human, in native-sequence or in variant form, and from any source, whether natural, synthetic, or recombinant. IGF-I has been isolated from human serum and produced recombinantly. See, e.g., EP 123,228 and 128,733.

Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

The preferred IGF-I variants are those described in U.S. Pat. No. 5,077,276 issued Dec. 31, 1991, in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1–3)-IGF-I, or des-IGF-I).

"High-affinity growth hormone binding protein" or "high-affinity GHBP" refers to the extracellular domain of the GH receptor that circulates in blood and functions as a GHBP in several species (Ymer and Herington, Mol. Cell. Endocrino., 41: 153 [1985]; Smith and Talamantes, Endocrinology, 123: 1489–1494 [1988]; Emtner and Roos, Acta Endocrinologica (Copenh.), 122: 296–302 [1990]), including man. Baumann et al., J. Clin. Endocrinol. Metab., 62: 134–141 (1986); EP 366,710 published 9 May 1990; Herington et al., J. Clin. Invest., 77: 1817–1823 (1986); Leung et al., Nature, 330: 537–543 (1987). A second BP with lower affinity for GH has also been described that appears to be structurally unrelated to the GH receptor. Baumann and Shaw, J. Clin. Endocrinol. Metab., 70: 680–686 (1990). Various methods exist for measuring functional GHBP in serum, with the preferred method being a ligand-mediated immunofunctional assay (LIFA) described by Carlsson et al., JCEM, 73: 1216 (1991) and U.S. Pat. No. 5,210,017.

Modes for Carrying Out the Invention:

The subpopulation of patients targeted for treatment by the current invention consists of those patients with partial growth hormone insensitivity syndrome as defined above. The patient must exhibit each of the clinical signs set forth to be treatable by the method claimed herein.

The GH and/or IGF-I is directly administered to the patient by any suitable technique, including parenterally, intranasally, intrapulmonary, orally, or by absorption through the skin. If they are administered together, they need not be administered by the same route. They can be administered locally or systemically. Examples of parenteral administration include subcutaneous, intramuscular, intravenous, intraarterial, and intraperitoneal administration. Preferably, they are administered by daily subcutaneous injection.

The GH and/or IGF-I to be used in the therapy will be formulated and dosed in a fashion consistent with good medical practice, taking into account the clinical condition of the individual patient (especially the side effects of treatment with GH or IGF-I alone), the site of delivery of the IGF-I and GH composition(s), the method of administration, the scheduling of administration, and other factors known to practitioners. The "effective amounts" of each component for purposes herein are thus determined by such considerations and are amounts that increase the growth rates of the patients.

If GH is administered alone, a dose of greater than 0.3 mg/kg/week is employed. Preferably, the dose of GH ranges from about 0.35 to 1.0 mg/kg/week, more preferably from about 0.5 to 0.7 mg/kg/week. In another preferred embodiment, the GH is administered once per day subcutaneously.

The GH is suitably administered continuously or non-continuously, such as at particular times (e.g., once daily) in the form of an injection of a particular dose, where there will be a rise in plasma GH concentration at the time of the injection, and then a drop in plasma GH concentration until the time of the next injection. Another non-continuous administration method results from the use of PLGA microspheres and many implant devices available that provide a discontinuous release of active ingredient, such as an initial burst, and then a lag before release of the active ingredient. See, e.g., U.S. Pat. No. 4,767,628, col. 2, lines 19–37.

The GH may also be administered so as to have a continual presence in the blood that is maintained for the duration of the administration of the GH. This is most preferably accomplished by means of continuous infusion via, e.g., mini-pump such as an osmotic mini-pump. Alternatively, it is properly accomplished by use of frequent injections of GH (i.e., more than once daily, for example, twice or three times daily).

In yet another embodiment, GH may be administered using long-acting GH formulations that either delay the clearance of GH from the blood or cause a slow release of GH from, e.g., an injection site. The long-acting formulation that prolongs GH plasma clearance may be in the form of GH complexed, or covalently conjugated (by reversible or irreversible bonding) to a macromolecule such as one or more of its binding proteins (WO 92/08985 published 29 May 1992) or a water-soluble polymer selected from PEG and polypropylene glycol homopolymers and polyoxyethylene polyols, i.e., those that are soluble in water at room temperature.

Alternatively, the GH may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides.

The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a $C_1$–$C_4$ alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The GH is covalently bonded via one or more of the amino acid residues of the GH to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the GH. It will be understood, however, that the type and amount of the reactive group chosen, as well as the type of polymer employed, to obtain optimum results, will depend on the particular GH employed to avoid having the reactive group react with too many particularly active groups on the GH. As this may not be possible to avoid completely, it is recommended that generally from about 0.1 to 1000 moles, preferably 2 to 200 moles, of activated polymer per mole of protein, depending on protein concentration, is employed. The final amount of activated polymer per mole of protein is a balance to maintain optimum activity, while at the same time optimizing, if possible, the circulatory half-life of the protein.

While the residues may be any reactive amino acids on the protein, such as one or two cysteines or the N-terminal amino acid group, preferably the reactive amino acid is lysine, which is linked to the reactive group of the activated polymer through its free epsilon-amino group, or glutamic or aspartic acid, which is linked to the polymer through an amide bond.

The covalent modification reaction may take place by any appropriate method generally used for reacting biologically active materials with inert polymers, preferably at about pH 5–9, more preferably 7–9 if the reactive groups on the GH are lysine groups. Generally, the process involves preparing an activated polymer (with at least one terminal hydroxyl group), preparing an active substrate from this polymer, and thereafter reacting the GH with the active substrate to produce the GH suitable for formulation. The above modification reaction can be performed by several methods, which may involve one or more steps. Examples of modifying agents that can be used to produce the activated polymer in a one-step reaction include cyanuric acid chloride (2,4,6-trichloro-S-triazine) and cyanuric acid fluoride.

In one embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the GH. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100°–110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxy-polyethylene glycolyl-N-succinimidyl glutarate, which can then be reacted with the GH. This method is described in detail in Abuchowski et al., *Cancer Biochem. Biophys.*, 7: 175–186 (1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., *Peptides: Synthesis-Structure-Function, Proceedings of the Seventh American Peptide Symposium*, Rich et al. (eds.) (Pierce Chemical Co., Rockford, Ill., 1981), p. 97–100, and in Nitecki et al., *High-Technology Route to Virus Vaccines* (American Society for Microbiology: 1986) entitled "Novel Agent for Coupling Synthetic Peptides to Carriers and Its Applications."

Specific methods of producing GH conjugated to PEG include the methods described in U.S. Pat. No. 4,179,337 on PEG-GH and U.S. Pat. No. 4,935,465, which discloses PEG reversibly but covalently linked to GH. Other specific methods for producing PEG-GH include the following:

PEGylation with methoxypolyethylene glycol aldehyde (Me-PEG aldehyde) by reductive alkylation and purification is accomplished by adding to 2 mg/mL of GH in PBS pH 7.0, 5 mM of Me-PEG aldehyde-5000 (molecular weight 5000 daltons) and 20 mM of NaCNBH3 and gently mixing at room temperature for 3 hours. Ethanolamine is then added to 50 mM to reductively amidate the remaining unreacted Me-PEG. The mixture is separated on an anion-exchange column, FPLC Mono Q. The surplus unreacted Me-PEG does not bind to the column and can then be separated from the mixture. Two main PEGylated GH fractions are obtained with apparent molecular weights of 30K and 40K on reduced SDS-PAGE, vs. 20K of the unreacted GH. GH-GHBP complex is PEGylated in the same manner to give a derivative of 150K by gel filtration.

PEGylation with N-hydroxysuccinimidyl PEG (NHS-PEG) and purification are accomplished by adding NHS-PEG at a 5-fold molar excess of the total lysine concentration of GH to a solution containing 2 mg/mL of GH in 50 mM of sodium borate buffer at pH 8.5 or PBS at pH 7, and mixing at room temperature for one hour. Products are separated on a Superose 12 sizing column and/or Mono Q of FPLC. The PEGylated GH varies in size depending on the pH of the reaction from approximately 300K for the reaction run at pH 8.5 to 40K for pH 7.0 as measured by gel filtration. The GH-GHBP complex is also PEGylated the same way with a resulting molecular weight of 400 to 600 Kd from gel filtration.

PEGylation of the cysteine mutants of GH with PEG-maleimide is accomplished by preparing a single cysteine mutant of GH by site-directed mutagenesis, secreting it from an *E. coli* 16C9 strain (W3110 delta tonA phoA delta E15 delta (argF-lac)169 deoC2 that does not produce the deoC protein and is described in U.S. Ser. No. 07/224,520 filed 26 Jul. 1988, now abandoned, the disclosure of which is incorporated herein by reference) and purifying it on an anion-exchange column. PEG-maleimide is made by reacting monomethoxyPEG amine with sulfo-MBs in 0.1M sodium phosphate pH 7.5 for one hour at room temperature and buffer exchanged to phosphate buffer pH 6.2. Next GH with a free extra cysteine is mixed in for one hour and the final mixture is separated on a Mono Q column as in Me-PEG aldehyde PEGylated GH.

As ester bonds are chemically and physiologically labile, it may be preferable to use a PEG reagent in the conjugating reaction that does not contain ester functionality. For example, a carbamate linkage can be made by reacting PEG-monomethyl ether with phosgene to give the PEG-chloroformate. This reagent could then be used in the same manner as the NHS ester to functionalize lysine side-chain amines. In another example, a urea linkage is made by reacting an amino-PEG-monomethyl ether with phosgene. This would produce a PEG-isocyanate that will react with lysine amines.

A preferred manner of making PEG-GH, which does not contain a cleavable ester in the PEG reagent, is described as follows: Methoxypoly(ethylene glycol) is converted to a carboxylic acid by titration with sodium naphthalene to generate the alkoxide, followed by treatment with bromoethyl acetate to form the ethyl ester, followed by hydrolysis to the corresponding carboxylic acid by treatment with sodium hydroxide and water, as reported by Büchmann et al., *Macromol. Chem.*, 182: 1379–1384 (1981). The resultant carboxylic acid is then converted to a PEG-N-hydroxysuccinimidyl ester suitable for acylation of GH by reaction of the resultant carboxylic acid with dicyclohexylcarbodiimide and NHS in ethyl acetate.

The resultant NHS-PEG reagent is then reacted with 12 mg/mL of GH using a 30-fold molar excess over GH in a sodium borate buffer, pH 8.5, at room temperature for one hour and applied to a Q Sepharose column in Tris buffer and eluted with a salt gradient. Then it is applied to a second column (phenyl Toyopearl) equilibrated in 0.3 M sodium citrate buffer, pH 7.8. The PEGylated GH is then eluted with a reverse salt gradient, pooled, and buffer-exchanged using a G25 desalting column into a mannitol, glycine, and sodium phosphate buffer at pH 7.4 to obtain a suitable formulated PEG7-GH.

The PEGylated GH molecules and GH-GHBP complex can be characterized by SDS-PAGE, gel filtration, NMR, tryptic mapping, liquid chromatography-mass spectrophotometry, and in vitro biological assay. The extent of PEGylation is suitably first shown by SDS-PAGE and gel filtration and then analyzed by NMR, which has a specific resonance peak for the methylene hydrogens of PEG. The number of PEG groups on each molecule can be calculated from the NMR spectrum or mass spectrometry. Polyacrylamide gel electrophoresis in 10% SDS is appropriately run in 10 mM Tris-HCl pH 8.0, 100 mM NaCl as elution buffer. To demonstrate which residue is PEGylated, tryptic mapping can be performed. Thus, PEGylated GH is digested with trypsin at the protein/enzyme ratio of 100 to 1 in mg basis at 37° C. for 4 hours in 100 mM sodium acetate, 10 mM Tris-HCl, 1 mM calcium chloride, pH 8.3, and acidified to pH<4 to stop digestion before separating on HPLC Nucleosil C-18 (4.6 mm×150 mm, 5µ,100A). The chromatogram is compared to that of non-PEGylated starting material. Each peak car then be analyzed by mass spectrometry to verify the size of the fragment in the peak. The fragment(s) that carried PEG groups are usually not retained on the HPLC column after injection and disappear from the chromatograph. Such disappearance from the chromatograph is an indication of PEGylation on that particular fragment that should contain at least one lysine residue. PEGylated GH may then be assayed for its ability to bind to the GHBP by conventional methods.

The various PEGylation methods used produced various kinds of PEGylated wild-type GH, with apparent molecular weights of 35K, 51K, 250K, and 300K by size exclusion chromatography, which should be close to their native hydrodynamic volume. These were designated PEG1-GH, PEG2-GH, PEG3-GH, and PEG7-GH, respectively. From the results of the tryptic mapping, the PEG1-GH and PEG2-GH both had the N-terminal 9-amino-acid fragment missing from the chromatogram and possibly PEGylated, which could be confirmed by the mass spectrometry of the big molecular species found in the flow-through of the liquid chromatograph. From the molecular weight on SDS-PAGE, PEG1-GH may have one PEG on the N-terminal amine, and the PEG2-GH may have two PEG molecules on the N-terminal amine, forming a tertiary amide. The PEG3-GH has about 5 PEG groups per molecule based upon the NMR result, and on the tryptic map, at least five peptide fragments were missing, suggesting that they are PEGylated. The PEG7-GH molecule is believed to have 6-7 PEG groups per molecule based on mass spectrometry.

The sites for adding PEG groups to GH, and those that are preferred residues for such conjugation, are N-terminal methionine or phenylalanine, lysine 38, lysine 41, lysine 70, lysine 140, lysine 145, lysine 158, and lysine 168. Two lysines that appeared not to be PEGylated were lysine 115 and lysine 172.

The GH is also suitably administered by sustained-release systems. Examples of sustained-release compositions useful herein include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers*, 22, 547–556 [1983]), poly(2-hydroxyethyl methacrylate) (Langer et al., *J. Biomed. Mater. Res.*, 15: 167–277 [1981], and Langer, *Chem. Tech.*, 12: 98–105 [1982]), ethylene vinyl acetate (Langer et al., supra) or poly-D-(−)-3-hydroxybutyric acid (EP 133,988), or PLGA microspheres. Sustained-release GH compositions also include liposomally entrapped GH. Liposomes containing GH are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese Pat. Appln. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy. In addition, a biologically active sustained-release formulation can be made from an adduct of the GH covalently bonded to an activated polysaccharide as described in U.S. Pat. No. 4,857,505 issued Aug. 15, 1989. In addition, U.S. Pat. No. 4,837,381 describes a microsphere composition of fat or wax or a mixture thereof and GH for slow release.

In another embodiment, the patients identified above are treated with an effective amount of IGF-I. As a general proposition, the total pharmaceutically effective amount of IGF-I administered parenterally per dose will be in the range of about 50 to 240 μg/kg/day, preferably 100 to 200 μg/kg/day, of patient body weight, although, as noted above, this will be subject to a great deal of therapeutic discretion. Also, preferably the IGF-I is administered once or twice per day by subcutaneous injection.

The IGF-I may be administered by any means, including injections (single or multiple, e.g., 1–4 per day) or infusions. As with the GH, the IGF-I may be formulated so as to have a continual presence in the blood during the course of treatment, as described above for GH. Thus, it may be covalently attached to a polymer or made into a sustained-release formulation as described above.

In addition, the IGF-I is appropriately administered together with any one or more of its binding proteins, for example, those currently known, i.e., IGFBP-1, IGFBP-2, IGFBP-3, IGFBP-4, IGFBP-5, or IGFBP-6. The IGF-I may also be coupled to a receptor or antibody or antibody fragment for administration. The preferred binding protein for IGF-I herein is IGFBP-3, which is described in U.S. Pat. No. 5,258,287 and by Martin and Baxter, *J. Biol. Chem.*, 261: 8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I may be accomplished by the method described in U.S. Pat. No. 5,187,151. Briefly, the IGF-I and IGFBP are administered in effective amounts by subcutaneous bolus injection in a molar ratio of from about 0.5:1 to about 3:1, preferably about 1:1.

In a further embodiment, both IGF-I and GH can be administered to the patient, each in effective amounts, or each in amounts that are sub-optimal but when combined are effective. Preferably such amounts are about 50 to 100 μg/kg/day of IGF-I and about 0.3 mg/kg/week GH. Preferably, the administration of both IGF-I and GH is by injection using, e.g., intravenous or subcutaneous means. More preferably, the administration is by subcutaneous injection for both IGF-I and GH, most preferably daily injections.

It is noted that practitioners devising doses of both IGF-I and GH should take into account the known side effects of treatment with these hormones. For GH, the side effects include sodium retention and expansion of extracellular volume (Ikkos et al., *Acta Endocrinol.* (Copenhagen), 32: 341–361 [1959]; Biglieri et al., *J. Clin. Endocrinol. Metab.*, 21: 361–370 [1961]), as well as hyperinsulinemia and hyperglycemia. The major apparent side effect of IGF-I is hypoglycemia. Guler et al., *Proc. Natl. Acad. Sci. USA*, 86: 2868–2872 (1989). Indeed, the combination of IGF-I and GH may lead to a reduction in the unwanted side effects of both agents (e.g., hypoglycemia for IGF-I and hyperinsulinism for GH) and to a restoration of blood levels of GH, the secretion of which is suppressed by IGF-I.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium, and/or non-ionic surfactants such as polysorbates, poloxamers, or PEG.

The IGF-I and GH are each typically formulated individually in such vehicles at a concentration of about 0.1 mg/mL to 100 mg/mL, preferably 1–10 mg/mL, at a pH of about 4.5 to 8. Full-length IGF-I is preferably formulated at a pH about 5–6, and des(1–3)-IGF-I is preferably formulated at a pH about 3.2 to 5. GH is preferably at a pH of 7.4–7.8. It will be understood that use of certain of the foregoing excipients, carriers, or stabilizers will result in the formation of IGF-I or GH salts.

While GH can be formulated by any suitable method, the preferred formulations for GH are as follows: For met-GH (Protropin® brand), the pre-lyophilized bulk solution contains 2.0 mg/mL met-GH, 16.0 mg/mL mannitol, 0.14 mg/mL sodium phosphate, 1.6 mg/mL sodium phosphate (monobasic monohydrate), pH 7.8. The 5-mg vial of met-GH contains 5 mg met-GH, 40 mg mannitol, and 1.7 mg total sodium phosphate (dry weight) (dibasic anhydrous), pH 7.8. The 10-mg vial contains 10 mg met-GH, 80 mg mannitol, and 3.4 mg total sodium phosphate (dry weight) (dibasic anhydrous), pH 7.8.

For metless-GH (Nutropin® brand), the pre-lyophilized bulk solution contains 2.0 mg/mL GH, 18.0 mg/mL mannitol, 0.68 mg/mL glycine, 0.45 mg/mL sodium phosphate, and 1.3 mg/mL sodium phosphate (monobasic monohydrate), pH 7.4. The 5-mg vial contains 5 mg GH, 45 mg mannitol, 1.7 mg glycine, and 1.7 mg total sodium phosphates (dry weight) (dibasic anhydrous), pH 7.4. The 10-mg vial contains 10 mg GH, 90 mg mannitol, 3.4 mg glycine, and 3.4 mg total sodium phosphates (dry weight) (dibasic anhydrous).

While the IGF-I can be formulated in any way suitable for administration, the preferred formulation contains about 2–20 mg/ml of IGF-I, about 2–50 mg/mL of an osmolyte, about 1–15 mg/mL of a stabilizer, and a buffered solution at about pH 5–5.5. Preferably, the osmolyte is an inorganic salt at a concentration of about 2–10 mg/mL or a sugar alcohol at a concentration of about 40–50 mg/mL, the stabilizer is benzyl alcohol or phenol, or both, and the buffered solution is an acetic acid salt buffered solution. More preferably, the osmolyte is sodium chloride and the acetic acid salt is sodium acetate. Even more preferably, the amount of IGF-I is about 8–12 mg/mL, the amount of sodium chloride is about 5–6 mg/mL, the amount of benzyl alcohol is about 8–10 mg/mL, the amount of phenol is about 2–3 mg/mL, and the amount of sodium acetate is about 50 mM so that the pH is about 5.4. Additionally, the formulation can contain about 1–5 mg/mL of a surfactant, preferably polysorbate or poloxamer, in an amount of about 1–3 mg/mL.

In addition, the IGF-I and GH, preferably the full-length IGF-I, may be formulated together in an appropriate carrier vehicle to form a pharmaceutical composition that preferably does not contain cells. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 7.4. If this mixture is to be stored, it is formulated in a buffer at a pH of about 6, such as citrate, with a surfactant that increases the solubility of the GE at this pH, such as 0.1% polysorbate 20 or poloxamer 188. The final preparation may be a stable liquid or lyophilized solid.

The preferred combined composition comprises IGF-I and GH in a weight ratio of IGF-I:GH of between about 1:1 and 100:1 (w/w), about 0.05–0.3 mM of an osmolyte, about 0.1–10 mg/mL of a stabilizer, about 1–5 mg/mL of a surfactant, and about 5–100 mM of a buffer at about pH 5–6. Preferably, the osmolyte is an inorganic salt and the surfactant is nonionic. More preferably, the inorganic salt is sodium chloride or potassium chloride, the stabilizer is phenol or benzyl alcohol, the surfactant is polysorbate or poloxamer, the buffer is sodium acetate or sodium citrate or both, and the amounts of IGF-I and GH are about 2–20 mg/mL and about 0.2–10 mg/mL, respectively, with the weight ratio of IGF-I:GH being between about 1:1 and 50:1. Even more preferably, the amount of IGF-I is about 5–10 mg/mL, the amount of GH is about 1–5 mg/mL, the weight ratio of IGF-I:GH is about 1:1 to 4:1, the amount of sodium chloride is about 5–7 mg/mL, the amount of phenol is about 0.1–3 mg/mL, the amount of benzyl alcohol is about 6–10 mg/mL, the surfactant is polysorbate in an amount of about 1–3 mg/mL, the amount of sodium acetate is about 2.5–4 mg/mL, and the amount of sodium citrate is about 0.1–1 mg/mL.

IGF-I and GH to be used for therapeutic administration are preferably sterile. Sterility is readily accomplished by filtration through sterile filtration membranes (e.g., 0.2 micron membranes). Therapeutic IGF-I and GH compositions generally are placed into a container having a sterile access port, for example, an intravenous solution bag or vial having a stopper pierceable by a hypodermic injection needle.

The IGF-I and GH ordinarily will be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered 1% (w/v) aqueous IGF-I and GH solutions, and the resulting mixture is lyophilized. The infusion solution is prepared by reconstituting the lyophilized IGF-I and GH using bacteriostatic Water-for-Injection.

The invention will be more fully understood by reference to the following examples. They should not, however, be construed as limiting the scope of the invention. All literature and patent citations are expressly incorporated by reference.

EXAMPLE I

In this example, serum concentrations of GHBP were measured in a large number of samples from short children with either defined etiologies of growth failure (GHD or TS) or ISS, and were compared to GHBP levels in normal controls.

Control subjects

To establish the normal range for GHBP in serum, samples from 773 children, 366 females and 407 males, were analyzed. Ages ranged from 3 to 16 years; in some cases, age for a given subject was reported to the nearest year. The majority of the samples were obtained from a normal, school-aged population through a screening program for detection of antibodies to pancreatic β-cells (Pasco Co. School System, Fla.), and additional samples were generously provided by Dr. Juan Sotos of Children's Hospital of Columbus, Ohio and Dr. Rebecca Kirkland of Baylor College of Medicine, Houston, Tex. The children were healthy and are believed to represent a cross-section of the American population with regard to stature.

Subjects with growth retardation

Serum samples from growth-retarded children (age 1 to 17 years) were collected at baseline evaluation of 776 subjects enrolled in a post-marketing surveillance project, the Genentech National Cooperative Growth Study (NCGS). Samples were provided by 106 of the centers participating in this study.

All children with GHD and ISS included for analysis had heights that were 2 or more SD below the mean for age and sex. Subjects were classified as GH deficient by their enrolling physician. None of the children with GHD had maximum stimulated or endogenous GH levels above 10 µg/L reported by the treating physician (using an unspecified assay) or measured at Genentech Inc. using a double monoclonal immunoradiometric assay (Tandem-R HGH, Hybritech, San Diego, Calif.). Excluded are subjects with organic causes of GHD, such as central nervous system (CNS) tumors.

Patients classified as ISS in the NCGS database were either designated as such by the enrolling physician (using various terms) or had a stimulated or endogenous GH level >10 µg/L with no organic etiology of short stature indicated. Patients with TS were so identified by their enrolling physicians and include those with various forms of mosaicism. None of the subjects included had previously received any form of GH therapy.

GHBP measurements

GHBP was measured by LIFA as described above. Briefly, ninety-six-well microtiter plates (Corning Glass Works, Corning, N.Y.) were coated with a monoclonal antibody directed against GHBP (MAb263, Agen, Australia) by incubating overnight at 4° C. with 100 µL/well of antibody at 10 µg/mL in 50 mmol/L carbonate buffer, pH 9.6. The coated wells were blocked with 150 µL PBS, pH 7.2, containing bovine serum albumin (BSA) (5 g/L) and washed. Standards (recombinant hGHBP) or samples (50 µL/well) were dispensed into the coated wells together with 50 µL/well of recombinant human GH (200 µg/L; Genentech, Inc.) and mouse immunoglobulin G (10 g/L; Fitzgerald Industries, Chelmsford, Mass.).

Plates were sealed, incubated at room temperature for 2 hr with gentle agitation, and washed before addition of a monoclonal anti-GH antibody (MAb MCB, Genentech, Inc.) conjugated to horseradish peroxidase (100 µL/well). After further incubation for 2 hours at room temperature, the plates were washed six times with wash buffer. Freshly prepared substrate solution (0.4 g of o-phenylenediamine dihydrochloride in one liter of phosphate-buffered saline plus 0.4 mL of 30% hydrogen peroxide) was added to the plates (100 µL per well) and the incubation carried out in the dark for 15 minutes at room temperature. The reaction was stopped by the addition of 100 µL of 2.25 mol/L sulfuric acid and the absorbance at 490 nm determined. The detection range in the LIFA was 15.6 to 1000 pmol/L. The intra- and interassay coefficients of variation were approximately 7% and 11%, respectively. All samples were measured in duplicate.

GH measurements

To assess spontaneous GH secretion in the different groups, GH concentrations were measured in serum samples taken at 20-minute intervals for 12 hours (8 pm to 8 am) from 851 of the children. Mean values were calculated for each subject. GH concentrations were measured using a monoclonal antibody-based immunoradiometric assay (IRMA), with a detection limit of 0.5 µg/L (Tandem-R HGH, Hybritech).

IGF-I measurements

IGF-I concentrations were measured in serum samples taken from 858 of the children at baseline at the time of overnight GH sampling, using RIA following acid ethanol extraction (IGF-I RIA Kit, Nichols Institute, San Juan Capistrano, Calif.).

Statistical analysis

Standardized height (SD score) was calculated from age- and sex-specific mean and standard deviations derived from the National Center for Health Statistics (NCHS) normative data for American children. Hamill et al., *Am. J. Clin. Nutrition*, 32: 607–629 (1979). Body mass index (BMI) was calculated utilizing the formula: weight (kg)/[height (m)]$^2$. Mean and SD values for age, height SD score, and BMI for growth-retarded children were calculated from data reported on NCGS enrollment forms.

Means and standard deviations for GHBP concentrations (Tables I and III) and for mean 12-hour GH concentrations (Table IV) were calculated after log transformation due to the skewed nature of the data. The antilogs of the mean, mean ±2 SD (GHBP, Table I) and mean ±1 SD (GHBP, Table III, and mean 12-hr GH, Table IV) were then calculated to provide the listed values. Effects of age and sex on log GHBP concentrations in the control group were assessed by analysis of variance (ANOVA).

The calculation of standardized GHBP levels (SD scores) was based on the means and associated SD's from the control subject data grouped by sex and age utilizing the equation below. For a GHBP concentration in an individual 3–15 years of age (the age range for which control samples were available), $$SD\ score = \frac{\log(GHBP) - \text{mean}(\log(GHBP)|age, sex)}{SD(\log(GHBP)|age, sex)}$$

where mean (log (GHBP)|age, sex) is the average log value of GHBP for control subjects of the same age and sex as that of the individual, and SD (log (GHBP)|age, sex) is the associated SD. After conversion to SD scores, the serum GHBP concentrations in children diagnosed with GHD, ISS, and TS were compared with each other and to controls of the same sex by ANOVA. The GHBP SD score was also calculated based on bone age, rather than chronological age.

When multiple between-group comparisons on any variable were performed, Bonferroni adjustments to the p-values for statistical significance were applied to maintain an overall 0.05 level of significance for the test. Nominal p-values for the significant statistical comparisons are included in the text.

Results

The normal range (mean ±2 SD) for serum GHBP concentrations in children between 3 and 15 years of age is shown in Table I. Due to a technical problem, results are not available for children 5 years of age. Both age and sex had a significant effect on GHBP concentrations. Females had higher GHBP concentrations than males (p<0.0001). In both sexes, GHBP concentrations increased with age (p<0.0001).

TABLE I

| Normal Range for Serum GHBP Concentration (pmol/L) | | | | | |
|---|---|---|---|---|---|
| Sex | Age | n | Mean − 2SD | Mean | Mean + 2SD |
| Male | 3 | 20 | 57 | 127 | 282 |
| " | 4 | 21 | 65 | 120 | 224 |
| " | 6 | 31 | 60 | 114 | 214 |
| " | 7 | 31 | 70 | 138 | 272 |
| " | 8 | 31 | 72 | 193 | 519 |
| " | 9 | 36 | 60 | 193 | 619 |
| " | 10 | 39 | 62 | 221 | 783 |
| " | 11 | 37 | 79 | 244 | 751 |
| " | 12 | 50 | 69 | 228 | 750 |
| " | 13 | 33 | 80 | 242 | 733 |
| " | 14 | 40 | 65 | 190 | 558 |
| " | 15 | 33 | 52 | 173 | 582 |
| Female | 3 | 15 | 77 | 149 | 288 |
| " | 4 | 17 | 62 | 179 | 519 |
| " | 6 | 32 | 58 | 144 | 358 |
| " | 7 | 32 | 71 | 172 | 419 |
| " | 8 | 32 | 92 | 230 | 572 |
| " | 9 | 34 | 96 | 214 | 477 |
| " | 10 | 35 | 72 | 247 | 844 |
| " | 11 | 32 | 98 | 289 | 849 |
| " | 12 | 36 | 86 | 226 | 595 |
| " | 13 | 35 | 110 | 306 | 856 |
| " | 14 | 34 | 111 | 271 | 660 |
| " | 15 | 32 | 103 | 316 | 965 |

Table II shows the mean (±SD) age, height SD score, and BMI for each group of subjects (height and BMI data were not available for all control subjects). Mean age was similar in all groups (approximately 11 years). Mean height SD scores were not statistically different among the GHD, ISS, and TS females or between the GHD and ISS males. Mean BMI values were significantly lower in the ISS groups compared with the other growth-retarded groups in both females (P≤0.0137) and males (p<0.0001).

TABLE II

| Age, height SD score, and BMI (mean ± SD) | | | | | |
|---|---|---|---|---|---|
| Etiology | Sex | n | Age (yr) | Height(SDS) | BMI |
| Control | M | 47 | 11.7 ± 2.8 | 0.3 ± 0.8 | 18.4 ± 2.9 |
| " | F | 35 | 11.6 ± 2.4 | 0.3 ± 0.8 | 19.0 ± 3.0 |
| GHD | M | 80 | 11.8 ± 3.6 | −2.9 ± 0.8 | 18.3 ± 4.5 |
| " | F | 27 | 10.8 ± 2.9 | −3.2 ± 0.9 | 17.8 ± 4.0 |
| TS | F | 96 | 11.5 ± 3.3 | −3.3 ± 0.9 | 19.1 ± 4.0 |
| ISS | M | 449 | 11.4 ± 3.4 | −2.9 ± 0.7 | 16.6 ± 2.3 |
| " | F | 124 | 10.8 ± 3.0 | −3.1 ± 0.7 | 16.4 ± 2.4 |

FIG. 1 shows serum GHBP concentrations in individual children with GHD, ISS, and TS compared to the normal range for the same sex (−2 SD to +2 SD). The corresponding mean GHBP concentrations and mean SD scores in all groups are listed in Table III. The figure shows that the patients who can be treated by the invention herein are those below the shaded area, provided that they also have the GH, IGF-I, and height requirements set forth as required in this subpopulation.

For males with either GHD or ISS, the mean GHBP SD score was lower than that of control males (both p<0.0001), and the mean SD score in males with ISS was lower than that of males with GHD (p<0.0001). The mean SD scores for females with ISS and GHD were lower than that of control females (p<0.0001 and p=0.0046, respectively). In addition, the mean SD score in ISS females was lower than that in GHD females (p=0.0039). When the GHD groups were limited to subjects with maximum stimulated GH levels ≦5 μg/L (n=23), the GHBP SD score was not significantly different from the control mean.

Because of differences in BMI between the GHD and ISS groups and the recognized relationship between BMI and GHBP levels, an analysis of covariance was performed using BMI as a covariate to determine if the between-group difference in GHBP was independent of differences in BMI. In both males and females, the differences in GHBP between the GHD and ISS groups remained significant (p<0.02).

In 91% of male ISS subjects and 92% of female ISS subjects, GHBP concentrations were below the mean for age- and sex-matched controls. The difference between ISS and GHD subjects was particularly striking in males, where 79 of 394 (20.1%) males with ISS had values >2 SD below the mean, compared with only 6 of 69 (8.7%) males with GHD.

In contrast to the females with GHD or ISS, the mean GHBP SD score in children with TS did not differ significantly from that of control females. GHBP SD scores computed for all growth-retarded groups using bone age rather than chronological age showed little difference (Table III).

TABLE III

| Serum GHBP Concentrations (pmol/L) | | | | | | | |
|---|---|---|---|---|---|---|---|
| Etiology | Sex | n | Mean | Mean −1 SD | Mean +1 SD | Mean GHBP SDS$_{CA}$ (n) | Mean GHBP SDS$_{BA}$ (n) |
| Control | M | 407 | 183 | 103 | 326 | 0.0 (402) | n/a |
| " | F | 366 | 228 | 133 | 394 | 0.0 (366) | n/a |
| GHD (GH<10) | M | 80 | 146 | 86 | 250 | −0.6 (69) | −0.5 (46) |
| GHD (GH<10) | F | 27 | 182 | 89 | 372 | −0.6 (26) | −0.5 (18) |
| GHD (GH<5) | M | 15 | 183 | 111 | 302 | 0.1 (12) | −0.2 (5) |
| GHD (GH<5) | F | 11 | 203 | 117 | 352 | −0.5 (11) | 0.1 (8) |
| TS | F | 96 | 208 | 115 | 378 | −0.3 (80) | −0.1 (61) |
| ISS | M | 449 | 103 | 63 | 166 | −1.2 (394) | −1.1 (244) |
| " | F | 124 | 131 | 81 | 213 | −1.2 (117) | −1.1 (67) | n/a - not available
CA - chronological age
BA - bone age

For mean GH concentrations obtained during 12-hour overnight GH sampling (Table IV), analysis of covariance with etiology, sex, and age revealed that only etiology had a significant impact on the mean 12-hour GH level. As expected, the mean value in children with GHD was significantly less than in controls (p<0.0001). The value in girls with TS was greater than that in GHD females (p<0.0001) and less than that in either ISS or control females (both p<0.002). The mean 12-hour GH concentration in subjects with ISS was not statistically different from that in the controls. However, ISS subjects with GHBP levels >2 SD below the mean had higher mean 12-hour GH values than those with normal GHBP levels (2.8 vs. 2.3 μg/L, p<0.005). Mean IGF-I levels were lowest in GHD patients, and were lower than controls for ISS and TS patients.

TABLE IV

| Etiology | Sex | Mean 12-hour GH and IGF-I Concentrations (µg/L) | | | | | | | |
|---|---|---|---|---|---|---|---|---|---|
| | | Mean 12-hr GH (µg/L) | | | | Extracted IGF-I (µg/L) | | | |
| | | n | Mean | Mean −1 SD | Mean +1 SD | n | Mean | Mean −1 SD | Mean +1 SD |
| Control | M | 47 | 2.1 | 1.2 | 3.5 | 47 | 217 | 130 | 363 |
| " | F | 35 | 2.7 | 1.4 | 5.1 | 35 | 308 | 178 | 531 |
| GHD (GH<10) | M | 79 | 1.4 | 0.9 | 2.1 | 80 | 99 | 41 | 238 |
| GHD (GH<10) | F | 26 | 1.2 | 0.7 | 2.0 | 27 | 84 | 36 | 195 |
| GHD (GH≦5) | M | 37 | 1.2 | 0.8 | 1.9 | 37 | 73 | 30 | 174 |
| GHD (GH≦5) | F | 15 | 1.0 | 0.6 | 1.6 | 16 | 74 | 31 | 175 |
| TS | F | 96 | 1.8 | 1.0 | 3.2 | 96 | 141 | 80 | 248 |
| ISS | M | 446 | 2.2 | 1.4 | 3.4 | 449 | 108 | 51 | 231 |
| " | F | 122 | 2.2 | 1.3 | 3.5 | 124 | 120 | 56 | 257 |

Serum GHBP concentrations in some children with ISS are lower than those in age-matched control children. Compared with control subjects, children with GHD also had lower GHBP concentrations, but the reduction was less pronounced than in children with ISS. In girls with TS, a condition where the diagnosis is based on the presence of a chromosomal abnormality and therefore is absolute, the GHBP levels were not different from those of the control group, indicating that the GHBP levels do not simply correlate with short stature.

In addition to geographically and genetically well-defined populations with impaired peripheral GH action, such as patients with Laron syndrome and African pygmies, there may be subjects with more subtle forms of GH insensitivity, most likely representing a variety of molecular defects. In spite of the probable heterogeneity of the causes of growth retardation in children with ISS, the results above show that as a group they have reduced serum GHBP concentrations, and a significant subset (20%) have GHBP levels 2 SD or more below the normal mean for age and sex.

The children with ISS that were studied did not differ from the control group in terms of GH secretion and had significantly lower GHBP concentrations than those of the group with GHD. Patients defined as GHD, based on the arbitrary cutoff of maximum GH<10 µg/L, had lower GHBP levels than controls. However, in GHD patients with maximum GH≦5 µg/L, mean GHBP SDS was greater than that of the GHD group with GH>5 µg/L and was not different from that of the controls.

EXAMPLE II

Figure 2:
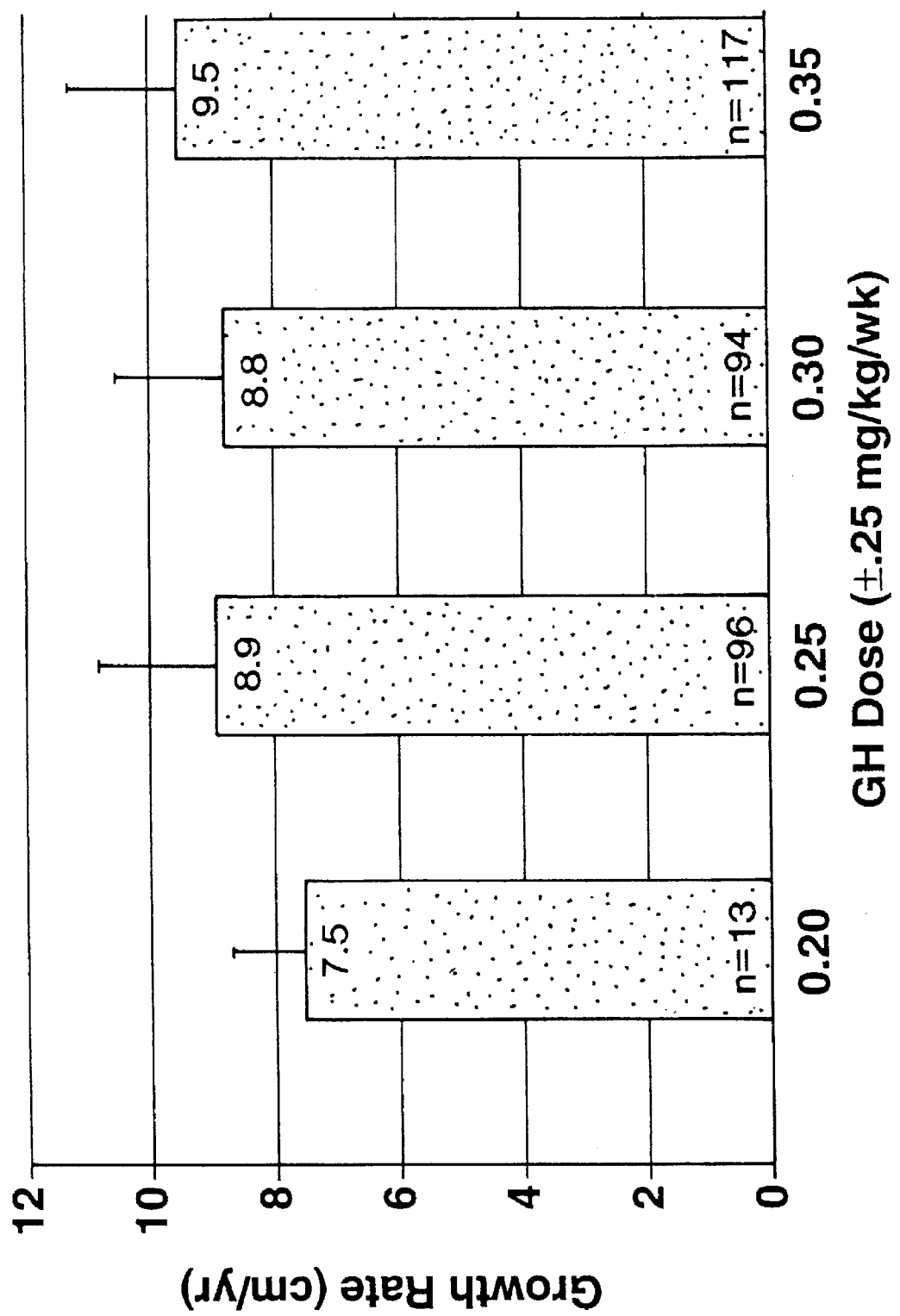
FIG. 2 shows the growth rate in cm/year of patients enrolled in the Genentech, Inc. National Cooperative Growth Study (NCGS) with ISS, treated with various weight-averaged doses of GH administered by daily injection.

Patients followed in a post-marketing surveillance study, the National Cooperative Growth Study (NCGS), were studied to compare growth rates for GHD patients with those for ISS patients treated with various average-weighted doses of GH. The ISS patients include both those with normal GHBP levels and those with low GHBP levels. The results for the ISS patients, shown in FIG. 2, demonstrate that a substantially higher growth rate was obtained for children treated with 0.35±0.025 mg/kg/week of GH as compared to 0.30 mg/kg/week or less. Comparison with the GHD patients reveals that the normal doses of GH of up to 0.30 mg/kg/week were not sufficient to allow patients to have a mean growth rate range close to that seen in the GHD patients, but that doses of 0.35±0.025 mg/kg/week result in a mean growth rate closer to the range seen in GHD patients (about 10 cm/year). Hence, a dose of GH of greater than 0.30 mg/kg/week is employed in the patients identified by this invention.

EXAMPLE III

Patients with ISS (as defined by a maximum GH level>10 µg/L and height SD score <−2) have low GHBP levels compared to normal controls as determined by LIFA. This was not the case in short children with GH deficiency or TS.

To assess the utility of the GHBP assay in the evaluation of short children, ISS patients were grouped according to their GHBP standard deviation score (SDS). Patients with low GHBP SDS, defined as <−2, were compared with patients with normal GHBP levels (GHBP SDS>−2) to determine whether there was evidence of impaired sensitivity to GH in the former group.

Patient Population

Serum samples were collected on 511 children with ISS who were subsequently treated with Protropin® brand GH and enrolled in the NCGS. To be included in this study, patients had to have a maximum GH>10 µg/L, height SDS≦−2, and no other reported etiology of short stature.

Assay Methods

GHBP was assayed using the LIFA, as described in Carlsson et al., supra. Monoclonal antibodies to GHBP (MAb 263, Agen, Australia) and GH (MAbMCB, Genentech, Inc., So. San Francisco, Calif.) were used. GHBP levels were standardized for age and sex using normative data for the LIFA based on samples provided by Dr. Thomas Merimee at University of Florida, Division of Endocrinology and Metabolism, Health Science Center, P.O. Box 100226, Gainesville, Fla. 32610-0226.

IGF-I was assayed following acid ethanol extraction (Nichols RIA Kit, San Juan Capistrano, Calif.) and mass units were converted to SD score for age and sex using reference data for this assay provided by Nichols Institute. GH samples obtained every 20 min for 12 hours overnight were all assayed by IRMA (Hybritech, Inc., San Diego, Calif.). Data for maximum stimulated GH were obtained from submitted samples using the Hybritech assay, as well as from tests reported by the physician using various GH assays.

Statistical Methods

Heights were standardized for age and sex, and weights were standardized for height and sex using published norms for North America. Hamill et al., *Am. J. Clin. Nutrition*, 32:

607–629 (1979). Mother's and father's height SDS were calculated based on normal adult standards. Hamill et al., supra.

After dividing the ISS patients into two groups based on their GHBP SD scores (≦–2 SD and >–2 SD), the two groups were compared to each other with respect to the means or medians of several co-variates (see Table VI). Univariate tests of significance between groups were performed using one of three tests: the t-test (for Gaussian-distributed variables), the Wilcoxon rank sum test (for non-Gaussian-distributed variables), or the Chi-square test (for categorical variables).

Multiple linear regression was used to determine which explanatory variables were linearly related to GHBP SDS, if any. Analysis of covariance (ANCOVA) was used to test for differences between the two GHBP groups after controlling for other significant variables.

Results

Enrollment information for the patients is presented in Table V, comparing the group with low GHBP levels (GHBP SD score ≦–2) with those with GHBP levels in the normal range. Patients in the low GHBP group were younger and had lower weight-for-height SDS and BMI than the normal GHBP group.

The mean height SD score was –2.9 in both groups, with values ranging from –5.8 to –2.0. Approximately three-fourths of the patients were male, similar to the distribution seen in the total NCGS database. Seventy-two percent of the patients were prepubertal at baseline. For analyses involving growth rate, only prepubertal patients were considered. It is concluded from the table that disorders of GH secretion are uncommon in patients with ISS, whereas some degree of GH insensitivity is present in some.

TABLE V

Baseline Patient Characteristics

| | GHBP SDS ≦ –2 | | | GHBP SDS > –2 | | | |
|---|---|---|---|---|---|---|---|
| | n | mean | SD | n | mean | SD | p-value |
| Male | 79 (78%) | | | 315 (77%) | | | 0.77 |
| Female | 22 (22%) | | | 95 (23%) | | | |
| Prepubertal | 75 (79%) | | | 279 (70%) | | | 0.085 |
| Pubertal | 20 (21%) | | | 119 (30%) | | | |
| Age (yr) | 101 | 10.5 | 3.1 | 410 | 11.4 | 2.8 | 0.0028 |
| Bone age (yr) | 63 | 7.9 | 3.1 | 243 | 9.0 | 3.0 | 0.011 |
| Bone age delay (yr) | 63 | 2.4 | 1.3 | 243 | 2.4 | 1.3 | 0.56 |
| Height SDS | 101 | –2.9 | 0.7 | 410 | –2.9 | 0.6 | 0.58 |
| Weight-for-Height SDS | 93 | –0.2 | 0.9 | 357 | 0.1 | 1.1 | 0.019 |
| Body mass index | 100 | 15.7 | 1.6 | 409 | 16.6 | 2.2 | 0.0007 |
| Mother's height SDS | 93 | –0.9 | 1.3 | 365 | –1.1 | 1.1 | 0.27 |
| Father's height SDS | 92 | –0.7 | 1.4 | 361 | –0.6 | 1.2 | 0.57 |

After dividing the patients into two groups based on GHBP SD scores, there were 101 patients with GHBP SDS≦2 (mean –2.5) and 410 patients with GHBP SDS>–2 (mean –0.9) (Table VI).

The two groups had comparable mean maximum GH levels; however, the use of various GH assays makes these values difficult to evaluate. The average for the mean 12-hour GH concentrations (using a single assay) was significantly higher in the low GHBP group (2.8 vs. 2.3 μg/L, p<0.0001), and the IGF-I SDS was significantly lower in that group (–3.3 vs. –2.5 μg/L, p<0.0001, Table VI).

Figure 3A:
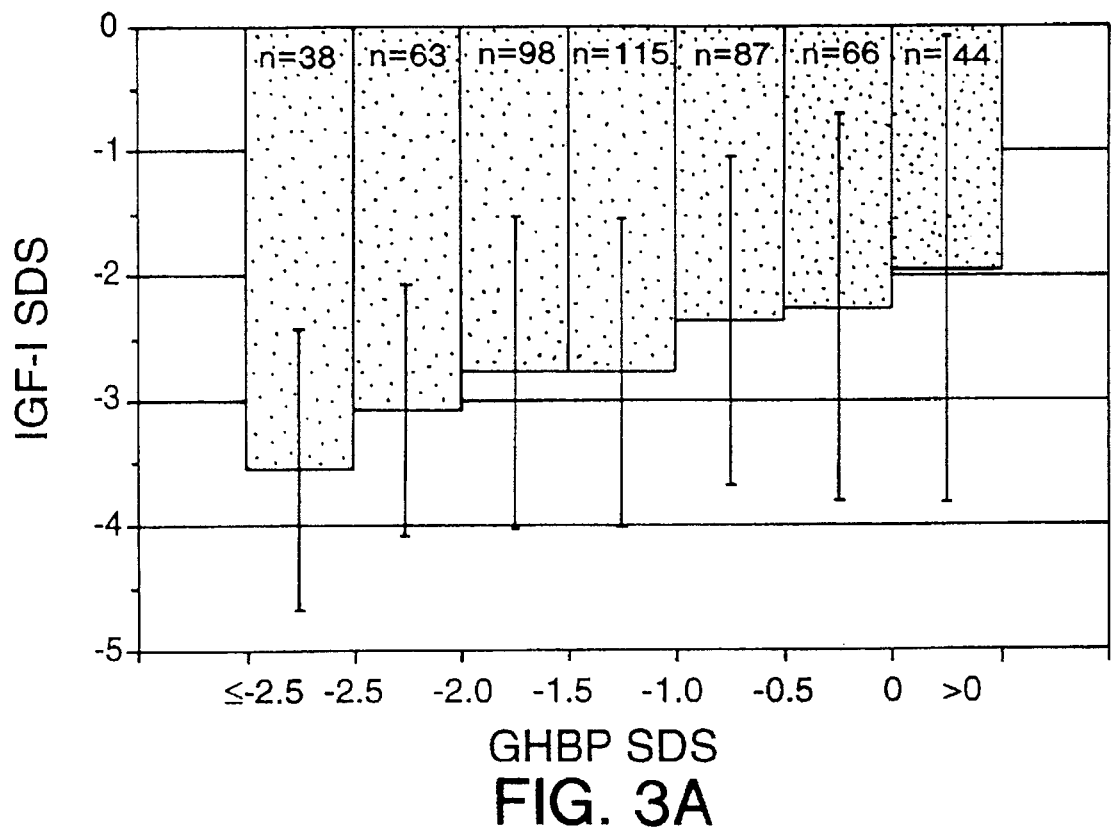
FIG. 3A depicts IGF-I concentrations, standardized for age and sex and expressed as SD score, by GHBP SD score (mean±SD).
Figure 3B:
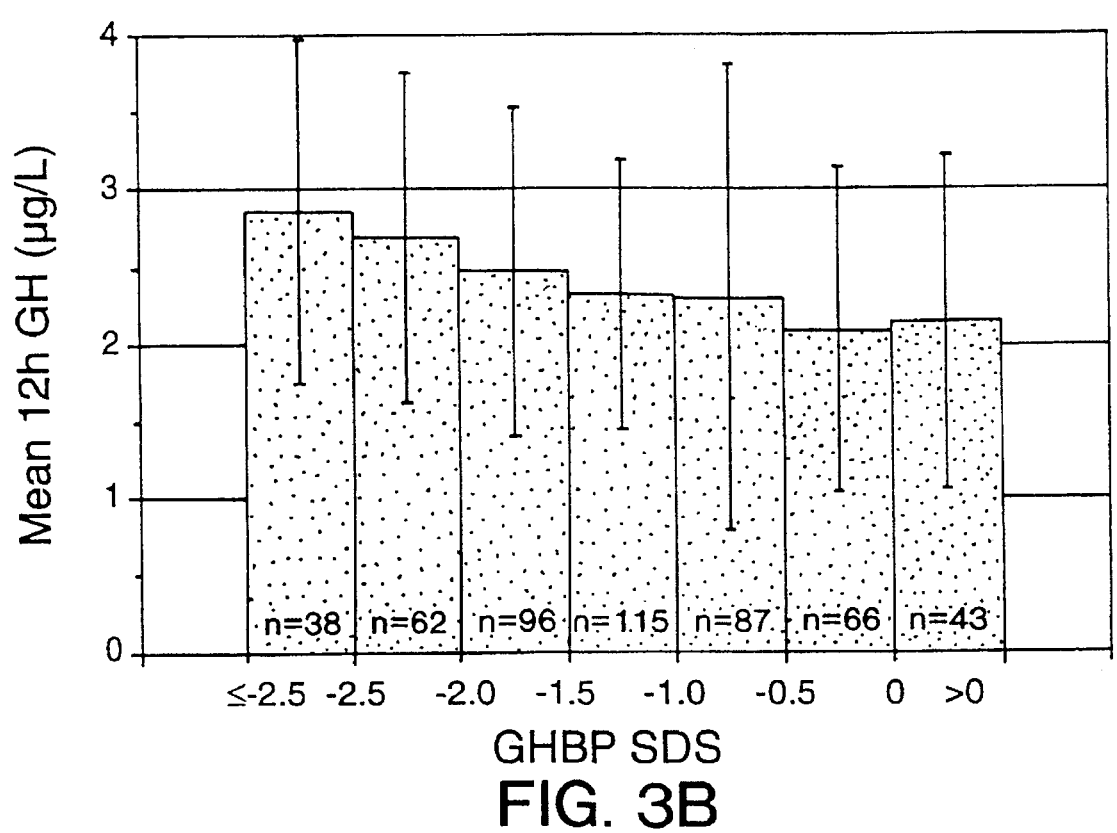
FIG. 3B depicts mean GH concentration from overnight sampling every 20 min for 12 hr, by GHBP SD score (mean±SD).

FIG. 3 shows that those with low GHBP SD scores had lower IGF-I SD scores (FIG. 3A) and higher mean 12-hour GH levels (FIG. 3B). GHBP SDS was positively correlated with IGF-I SDS (r=0.274) and negatively correlated with mean 12-hour GH (r=–0.17).

Using analysis of covariance, controlling for differences in age, weight-for-height SDS, and mean 12-hour GH, ISS patients with GHBP SDS≦–2 still had significantly lower IGF-I SDS than those with GHBP SDS>–2 (p=0.0001). Similarly, the low GHBP group had significantly higher mean 12-hour GH than the normal GHBP group (p=0.0001) after controlling for age, weight-for-height SDS, and IGF-I SDS.

TABLE VI

GHBP, IGF-I and mean 12-hr GH Concentrations (mean ± SD)

| | GHBP SDS ≦ –2 (n = 101) | GHBP SDS > –2 (n = 410) | p-value |
|---|---|---|---|
| GHBP (pmol/L) | 60 ± 14 | 138 ± 68 | <0.0001 |
| GHBP SDS | –2.5 ± 0.4 | –0.9 ± 0.8 | <0.0001 |
| IGF-I (μg/L) | 100 ± 61 | 149 ± 101 | <0.0001 |
| IGF-I SDS | –3.3 ± 1.1 | –2.5 ± 1.4 | <0.0001 |
| Mean 12-hr GH (μg/L) | 2.8 ± 1.1 | 2.3 ± 1.1 | <0.0001 |
| Maximum GH (μg/L) | 15.7 ± 8.2 | 15.5 ± 10.0 | 0.309 |

Mean pre-treatment growth rates were approximately 4 cm/yr regardless of GHBP SD score, although these rates were slightly greater in those with GHBP levels close to the normal mean. Mean growth rate during the first year of GH therapy was approximately 8 cm/yr and did not correlate with GHBP SD score. FIG. 4 shows first-year growth rates for pre-pubertal patients plotted against their weighted average GH dose. Although there was a trend for higher growth rates with higher GH dose, there was no statistically significant correlation.

Table VII compares the growth rate data for patients with low GHBP levels with those with GHBP levels in the normal range. The two groups had comparable mean GH dose and injection schedules. There were no significant differences between the groups for pretreatment growth rate or growth rates during the first four years of GH therapy. The mean change in height SD score was comparable in the two groups, with a mean increase of 1.4 in those followed for four years in both groups.

TABLE VII

Growth Rate and Change in Height SD Score on GH Therapy

| | GHBP SDS ≦ –2 (n = 101) | | | GHBP SDS > –2 (n = 410) | | | |
|---|---|---|---|---|---|---|---|
| | n | mean | SD | n | mean | SD | p-value |
| GH Dose (mg/kg · wk) | 64 | 0.272 | 0.052 | 262 | 0.277 | 0.061 | 0.91 |
| Schedule (inj./wk) | 49 | 3.8 | 1.6 | 231 | 3.4 | 1.1 | 0.03 |

TABLE VII-continued

Growth Rate and Change in Height SD Score on GH Therapy

| | GHBP SDS ≦ -2 (n = 101) | | | GHBP SDS > -2 (n = 410) | | | |
|---|---|---|---|---|---|---|---|
| | n | mean | SD | n | mean | SD | p-value |
| Growth Rate (cm/yr) | | | | | | | |
| Pretreatment | 76 | 4.0 | 1.9 | 285 | 4.3 | 2.1 | 0.70 |
| 1st Year | 60 | 8.2 | 1.5 | 258 | 8.4 | 1.9 | 0.42 |
| 2nd Year | 45 | 8.0 | 1.8 | 150 | 7.8 | 1.8 | 0.74 |
| 3rd Year | 38 | 7.6 | 1.9 | 94 | 7.7 | 3.0 | 0.66 |
| 4th Year | 25 | 6.8 | 1.9 | 50 | 6.1 | 1.6 | 0.18 |
| Δ Height SDS | | | | | | | |
| 1st Year | 71 | 0.5 | 0.3 | 284 | 0.4 | 0.3 | 0.6 |
| 2nd Year | 62 | 0.8 | 0.4 | 210 | 0.8 | 0.5 | 0.5 |
| 3rd Year | 49 | 1.2 | 0.5 | 143 | 1.2 | 0.6 | 0.5 |
| 4th Year | 31 | 1.4 | 0.5 | 79 | 1.4 | 0.6 | 0.7 |

Although 12-hour serial sampling profiles for GH were obtained on all of the ISS children in this study, they were found to have normal mean levels, suggesting that neurosecretory dysfunction was not present in most of the patients. The mean 12-hour GH levels showed a negative correlation with mean GHBP SD score, as has been described in normal individuals. Martha et al., *J. Clin. Endocrinol. Metab.*, 73: 175–181 (1991). However, IGF-I SDS was positively correlated with GHBP SD score. The patients with lower GHBP levels had higher GH yet lower IGF-I levels, consistent with growth hormone insensitivity.

A significant predictor of GHBP concentration is the body mass index, which was assessed using weight standardized for height and age. It was found that the relationship described for GHBP, GH, and IGF-I in the ISS patients remained significant in an analysis of covariance after controlling for age and weight-for-height SDS.

Figure 5:
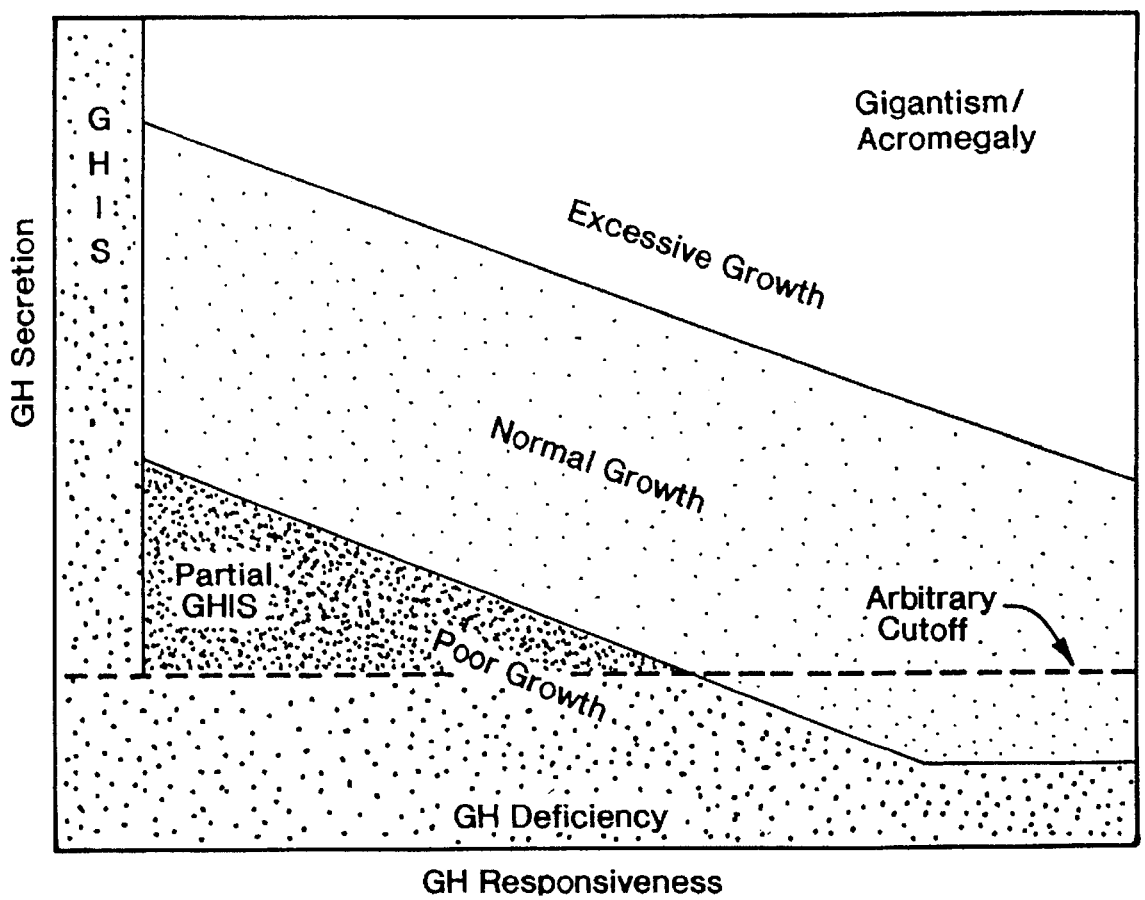
FIG. 5 shows growth status as predicted by a measure of GH secretion (e.g., stimulated or endogenous GH concentration) vs. a measure of GH responsiveness (e.g., GHBP concentration).

The growth data available for these patients through the NCGS database revealed no correlation of baseline growth rate or height SD score with GHBP SD score. Moreover, there was no significant correlation of GHBP SD score to growth response to growth hormone therapy. Without being limited to any one theory, one possible explanation is illustrated schematically in FIG. 5. Since GP secretion and GHBP levels appear to be negatively correlated in normally growing children (Martha et al., supra), a normal range can be proposed as depicted in the figure showing GH secretion vs. GH responsiveness. Those with excessive GH relative to their GHBP levels would be expected to demonstrate excessive growth, while those whose GH levels are too low for their GHBP levels would have poor growth. Since the current definition of GH deficiency is arbitrarily defined and based solely on measures of GH secretion, there may be some patients with GH levels above this threshold which are inadequate for their low GHBP levels, resulting in poor growth.

In conclusion, ISS patients with low GHBP levels, compared with those with normal GHBP levels, had lower IGF-I levels and higher mean 12-hour GH levels, suggesting partial GH insensitivity. Administering to this subset of patients exogenous GH beyond the normal amount would be expected to raise their circulating GH to levels more appropriate for their GHBP levels, thus overcoming their partially resistant state.

EXAMPLE IV

Nine children with moderate/severe short stature [selection criteria: height standard deviation score of <-2, mean stimulated GH>10 ng/mL, GHBP<-2 SD, and IGF-I<-2 SD] were studied to determine whether their short stature is due to mutations in the growth hormone receptor (GHR) gene. These children did not have the phenotypic features of Laron syndrome and were partially responsive to exogenous recombinant GH at 0.3 mg/kg/week given once daily by subcutaneous injection. These patients were selected based on five main parameters, choosing the scoring of 3 in each instance with a maximum score of 12, as follows:

| Parameter | Score = 1 | Score = 2 | Score = 3 |
|---|---|---|---|
| Maximum stimulated GH | >10 | >15 | >20 |
| IGF-I SDS | <-2 | <-3 | <-4 |
| GHBP SDS | <-2 | <-2.5 | <-3 |
| Height SDS | <-2.5 | <3.5 | — |
| Pre-treatment Growth Rate | <4 | — | — |

DNA and RNA were extracted from Epstein Barr Virus-transformed lymphocytes, and exons 2–10 of the GHR gene were amplified by polymerase chain reaction (PCR) directly from genomic DNA or from cDNA synthesized by reverse transcriptase treatment of RNA. Amplified sequences were examined for subtle mutations by the technique of single-stranded conformational polymorphism (SSCP) analysis on MDE gels (G. T. Baker) with 1%, 4%, or 10% glycerol. Orita et al., *Genomics*, 5: 874–879 (1989); Soto and Sukumar, *PCR Meth. Appl.*, 2: 96–98 (1992). SSCP analysis relies on differences in secondary structure assumed by single-stranded DNA molecules that differ by as little as a single base change. These differences in secondary structure result in variation in electrophoretic mobility in non-denaturing acrylamide-based gels. The efficiency of detecting mutations with SSCP analysis varies from approximately 90% for fragments under 200 base pairs in size to 70–80% for the 200 to 400 base pair size range. Prosser, *Tibtech*, 11: 238–246 (1993). GHR defects were detected as aberrant bands on SSCP gels in four of the nine children. No abnormalities were detected in the GHR locus in seven control children with intrauterine growth retardation.

The GHR alleles in two patients have been characterized in detail by DNA sequencing. Patient 4 carries two independent missense mutations in the GHR gene which were detected by SSCP; each mutation affects one of the two alleles of the gene (FIG. 6). In exon 4, a G→A transition mutation at nucleotide 48 converts a glutamic acid (residue 44 in the mature peptide) to lysine (FIG. 6, allele 2). A similar mutation generated by substituting an alanine for this glutamic acid residue caused a three-fold reduction in GH binding in a competitive-displacement, single-site binding assay. Bass et al., *Proc. Natl. Acad. Sci. USA*, 88: 4498–4502 (1991). The glutamic acid to lysine substitution is a more dramatic change and would be expected to disrupt hormone binding to a greater extent. Indeed, the results suggest an approximate 500-fold reduction in site 1 binding for this mutation.

The second allele in this patient carries a C→T transition mutation at nucleotide 96 in exon 6 (FIG. 6, allele 1). This mutation results in the substitution of the arginine at position 161 in the mature peptide with a cysteine residue. The functional significance of introducing an additional cysteine residue to the extracellular domain of the receptor is not known yet with certainty, but without being limited to any one theory, it is believed that the presence of the cysteine could disrupt the secondary structure of the receptor and thereby influence its ability to bind GH or may affect the ability of the receptor to dimerize. A similar mutation in which arginine 161 was replaced with alanine showed a 2.5-fold reduction in binding to GH. In the family of Patient 4, the mutation causing the glutamic acid to lysine change (E44K) has been transmitted from the paternal grandmother to father to the proband, and the second mutation causing the arginine to cysteine change (R161C) has been transmitted from the proband's mother.

In Patient 2, one allele of the GHR gene produces a truncated protein due to the introduction of a stop codon after residue 216 of the mature peptide (FIG. 7). A T→A transversion mutation at nucleotide 152 in exon 5 (which was detected by SSCP analysis) converts a codon encoding cysteine into one encoding a stop. The detection of very low levels of GHBP in this patient suggests the presence of a second mutation affecting the other GHR allele in this patient. This second mutation has not been detectable by SSCP analysis, but given that the efficiency of mutation detection by SSCP is less than 100%, the presence of a second mutation in the GHR gene in this patient has not been ruled out.

In further support that the low GHBP level in Patient 2 is likely due to defects in both alleles, Fielder et al., *J. Clin. Endocrinol. Metab.*, 74: 743–750 (1992) concluded that the GHBP levels in the mothers and fathers (who should be heterozygous) were not significantly different from the controls, i.e., if only one allele is affected the heterozygotes could not be distinguished from the controls based on their GHBP levels.

An additional two patients have shown aberrant bands by SSCP analysis. In the third patient an aberrant band was observed in the exon 7 PCR products. The fourth patient carries an alteration in exon 4 that was apparent on SSCP analysis.

These data suggest that heterogeneous GHR defects may be the cause of poor growth in a subset of non-GH-deficient short stature patients. These GHR defects are presumably milder than those observed in complete GH-insensitivity (Laron) syndrome and provide a molecular basis for at least some cases of non-GH-deficient short stature.

EXAMPLE V

Eighty prepubertal children diagnosed as having an average height less than −2 standard deviations below normal height, serum levels of GHBP and IGF-I that are at least 2 standard deviations below normal levels, and a mean or maximum stimulated serum level of GH that is at least normal, aged 5–12, are treated as follows: 20 with IGF-I alone, 20 with GH alone, 20 with GH and IGF-I together, and 20 with placebo. When the drugs are given alone, the IGF-I is administered once per day by subcutaneous injection at a dose of 150 µg/kg/day and the GH is administered once per day by subcutaneous injection at a dose of 100 µg/kg/day (0.7 mg/kg/week). When the drugs are combined, the IGF-I is administered once per day by subcutaneous injection at a dose of 75 µg/kg/day and the GH is administered once per day by subcutaneous injection at a dose of 50 µg/kg/day (0.35 mg/kg/week). The IGF-I formulation is either (a) 10 mg/ml of IGF-I in 20 mM sodium acetate buffer, 2.5 mg/ml (0.25%) phenol, 45 mg/ml mannitol, pH 5.0; or (b) 10 mg/ml of IGF-I in S0 mM sodium acetate buffer, 2.5 mg/ml phenol, 5.84 mg/ml NaCl, and 9 mg/ml benzyl alcohol, pH 5.4. The GH formulation is either Nutropin® or Protropin® brand GH available from Genentech, Inc. The patients are treated for 6 months with this protocol. The increase in height of each patient is measured.

This study shows that IGF-I or high-dose GH or the combination would be expected to increase the growth rates of all the patients as compared to those patients treated with placebo.

Alternative designs for clinical trials are as follows:

The same groups and subclass of children are treated in the same mode with GH alone at 50 µg/kg/day or 100 µg/kg/day, or IGF-I alone at 75, 100, 150, or 200 µg/kg/day. For the combination treatment, GH is used at 50 µg/kg/day and IGF-I at 75 or 100 µg/kg/day with or without using a placebo for comparison.

---

What is claimed is:

1. A method for increasing the growth rate of a human patient having partial growth hormone insensitivity syndrome comprising administering an effective amount of growth hormone that increases the growth rate of the patient to said patient, whereby said patient has a height less than about −2 standard deviations below normal for age and sex, and has serum levels of high-affinity growth hormone binding protein and IGF-I that are at least 2 standard deviations below normal levels and has a mean or maximum stimulated serum level of growth hormone that is at least normal, wherein the patient does not have Laron syndrome.

2. The method of claim 1 wherein the amount of growth hormone ranges from about 0.35 to 1.0 mg/kg/week.

3. The method of claim 1 wherein the growth hormone is administered once per day.

4. The method of claim 3 wherein the growth hormone is administered by subcutaneous injections.

5. The method of claim 1 wherein the growth hormone is formulated at a pH of 7.4 to 7.8.

6. The method of claim 1 wherein the patient has a heterogeneous GHR gene defect.

7. A method for increasing the growth rate of a human patient with non-GH-deficient short stature but not Laron syndrome comprising detecting whether the patient has a height less than about −2 standard deviations below normal for age and sex, and has serum levels of high-affinity growth hormone binding protein and IGF-I that are at least 2 standard deviations below normal levels and has a mean or maximum stimulated serum level of growth hormone that is at least normal, and, if so, administering an effective amount of growth hormone that increases the growth rate of the patient to said patient.

8. The method of claim 7 wherein the detecting step also determines whether the patient has a heterogeneous GHR gene defect.

* * * * *